United States Patent
LeBlanc et al.

(10) Patent No.: US 9,155,332 B2
(45) Date of Patent: Oct. 13, 2015

(54) RETORT WITH PROGRESSIVE LATCH, ROLLER SUPPORT ARRANGEMENT AND METHOD AND SYSTEM FOR RECIPROCATION OF LOADS

(75) Inventors: Philip M. LeBlanc, Franklinton, LA (US); Beau R. Moreau, Lacombe, LA (US)

(73) Assignee: ALLPAX PRODUCTS LLC, Covington, LA (US)

( * ) Notice: Subject to any disclaimer, the term of this patent is extended or adjusted under 35 U.S.C. 154(b) by 250 days.

(21) Appl. No.: 13/569,748

(22) Filed: Aug. 8, 2012

(65) Prior Publication Data
US 2013/0039807 A1 Feb. 14, 2013

Related U.S. Application Data

(60) Provisional application No. 61/522,052, filed on Aug. 10, 2011.

(51) Int. Cl.
*A23L 3/00* (2006.01)
*A23L 3/12* (2006.01)
*A23L 3/14* (2006.01)
*A23L 3/10* (2006.01)
*A61L 2/26* (2006.01)

(52) U.S. Cl.
CPC ... *A23L 3/12* (2013.01); *A23L 3/14* (2013.01); *A23L 3/10* (2013.01); *A61L 2/26* (2013.01)

(58) Field of Classification Search
CPC ............... A23L 3/10; A23L 3/14; A61L 2/06
USPC ............... 99/369, 371, 367, 364, 359, 443 C, 99/443 R, 478; 422/38, 26
See application file for complete search history.

(56) References Cited

U.S. PATENT DOCUMENTS

| | | | |
|---|---|---|---|
| 861,120 A | 3/1906 | Guibbini | |
| 915,428 A | 3/1909 | Gubbini | |
| 1,010,805 A | 12/1911 | Rogers | |
| 1,491,031 A | 4/1924 | Chapman | |
| 1,636,768 A | 7/1927 | Ford | |
| 1,709,175 A | 4/1929 | Huygen | |
| 1,975,073 A | 10/1934 | Chapman | |
| 2,052,096 A | 8/1936 | Kronquest | |
| 2,086,241 A | 7/1937 | Schaerr | |
| 2,134,817 A * | 11/1938 | Gerber | 99/367 |

(Continued)

FOREIGN PATENT DOCUMENTS

| | | |
|---|---|---|
| DE | 3628012 | 2/1988 |
| EP | 0512261 A | 4/1992 |

(Continued)

OTHER PUBLICATIONS

PCT US2012/049699, International Search Report and Written Opinion, Mailed Jan. 8, 2013, 11 pages.

*Primary Examiner* — Reginald L Alexander
*(74) Attorney, Agent, or Firm* — Thompson Hine LLP

(57) ABSTRACT

A retort system for heating product to a specified temperature for sterilization is provided. The system includes a vessel having an associated heating system. A frame within the vessel for securing the baskets during reciprocation of the baskets may include a progressive latch mechanism. A roller arrangement for supporting baskets within the vessel may include both a plurality of transfer rollers and a plurality of support rollers.

17 Claims, 23 Drawing Sheets

(56) References Cited

U.S. PATENT DOCUMENTS

| | | | |
|---|---|---|---|
| 2,499,203 A | 2/1950 | Warren | |
| 3,291,289 A | 12/1966 | Savage | |
| 3,370,727 A * | 2/1968 | Shaw | 414/495 |
| 3,511,169 A | 5/1970 | Fritzberg et al. | |
| 3,696,912 A * | 10/1972 | Fleischauer et al. | 198/781.1 |
| 3,785,468 A * | 1/1974 | Misenheimer | 193/35 MD |
| 4,003,302 A | 1/1977 | Mencacci et al. | |
| 4,170,421 A | 10/1979 | Balding et al. | |
| 4,348,912 A | 9/1982 | Thomas | |
| 4,632,026 A | 12/1986 | Yamamoto et al. | |
| 4,708,053 A | 11/1987 | Forsythe et al. | |
| 4,748,816 A | 6/1988 | Arfert et al. | |
| 4,929,087 A | 5/1990 | Brigolle | |
| 5,056,642 A * | 10/1991 | Highsmith | 193/35 R |
| 5,626,824 A | 5/1997 | Ishikawa et al. | |
| 5,687,639 A * | 11/1997 | Planck et al. | 99/369 |
| 5,836,204 A | 11/1998 | Skak | |
| 5,857,312 A | 1/1999 | Walden | |
| 6,605,252 B2 | 8/2003 | Omasa | |
| 6,739,108 B2 | 5/2004 | Blattner et al. | |
| 6,745,664 B2 | 6/2004 | Kopkie | |
| 7,188,993 B1 | 3/2007 | Howie | |
| 7,712,202 B2 | 5/2010 | Greve | |
| 8,262,987 B2 * | 9/2012 | Tago et al. | 422/38 |
| 2003/0081499 A1 | 5/2003 | Friedman | |
| 2007/0258850 A1 | 11/2007 | Miller, III et al. | |
| 2007/0292570 A1 | 12/2007 | Walden et al. | |

FOREIGN PATENT DOCUMENTS

| | | |
|---|---|---|
| EP | 1050366 A | 8/2000 |
| EP | 1151757 B | 11/2004 |

* cited by examiner

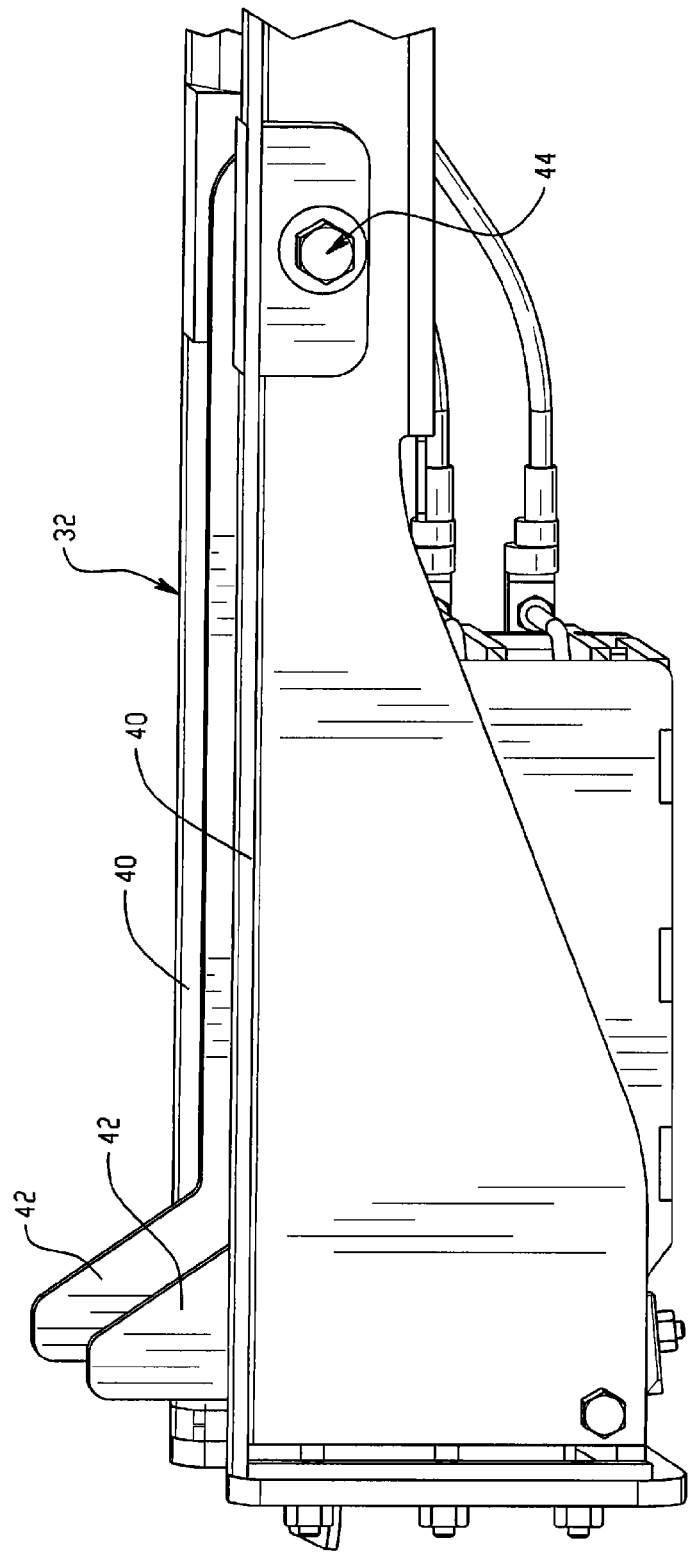

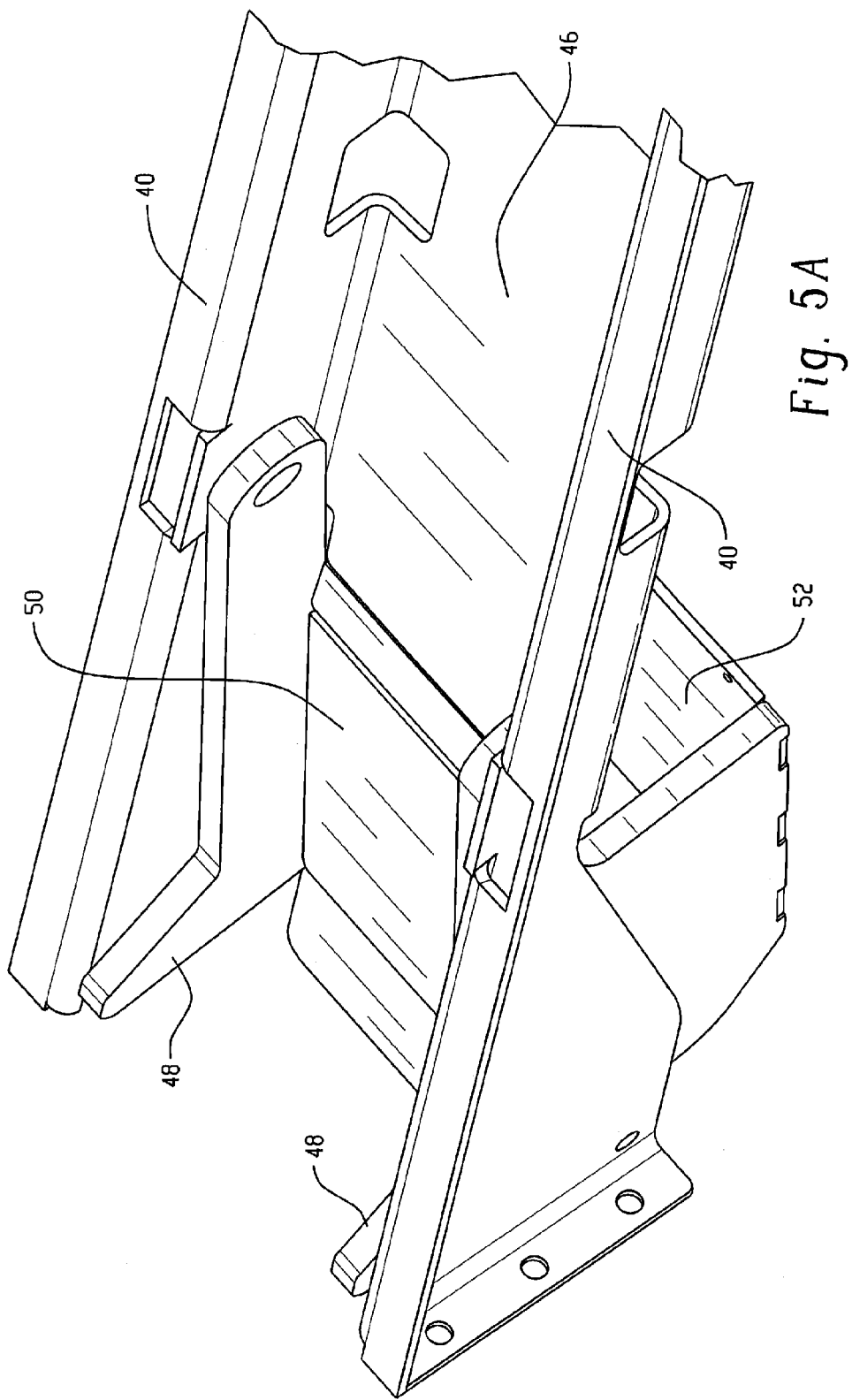

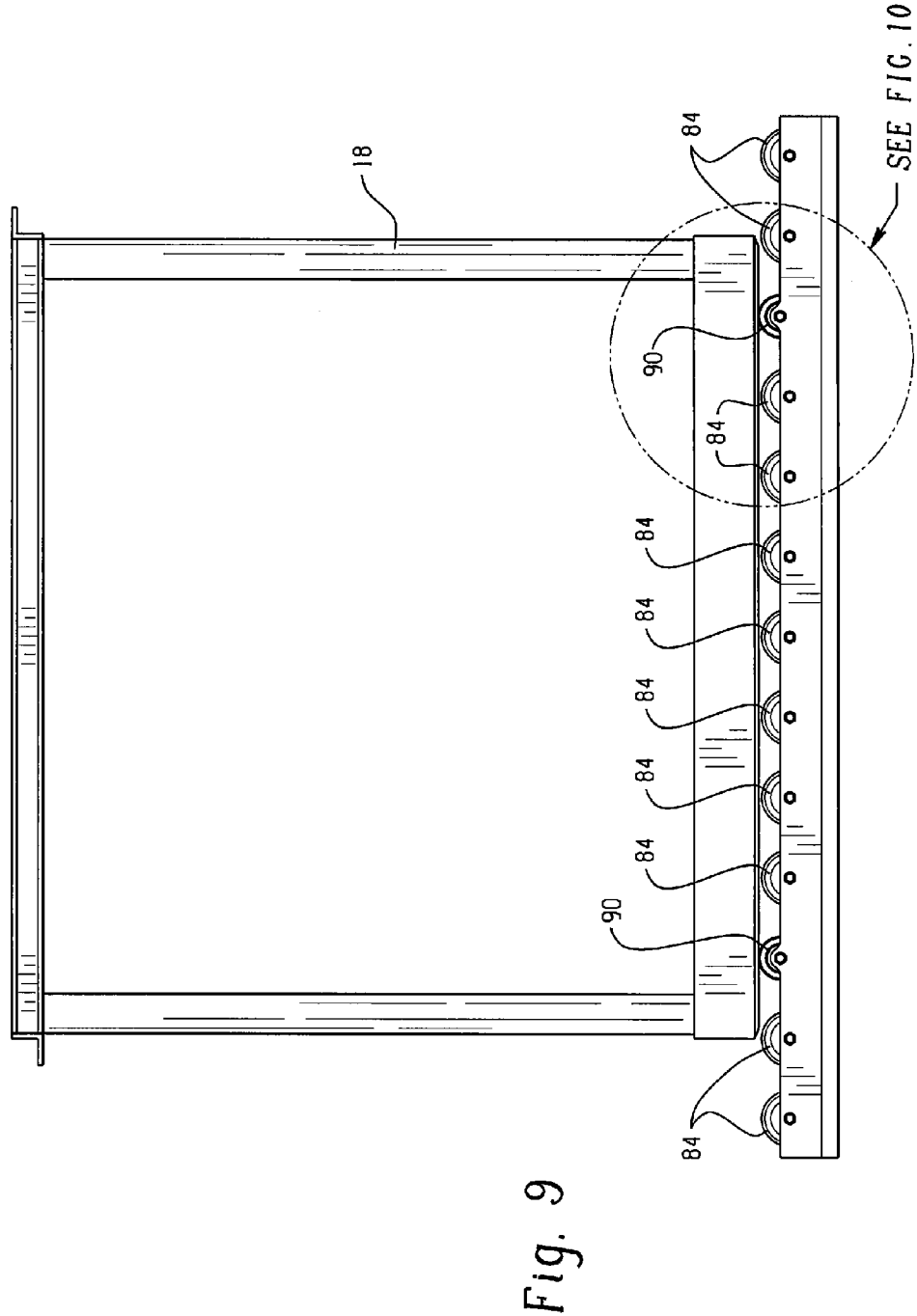

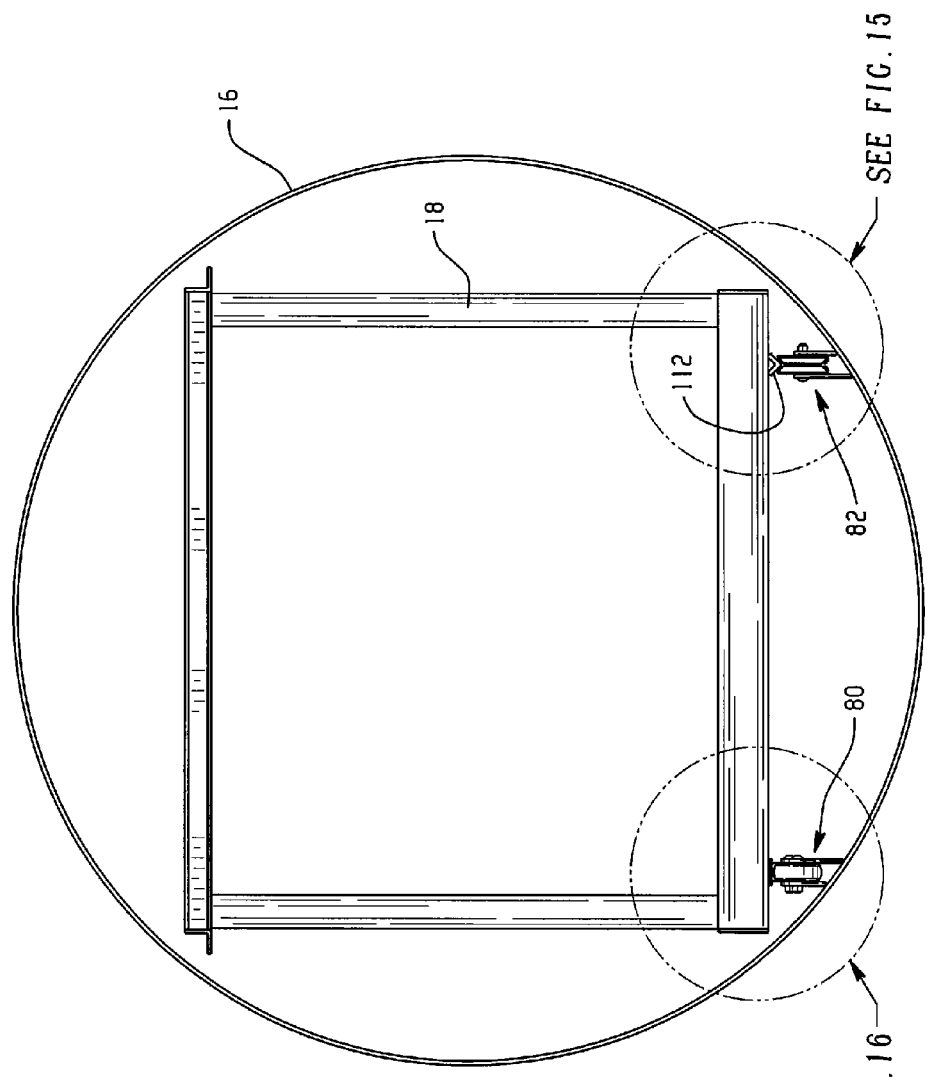

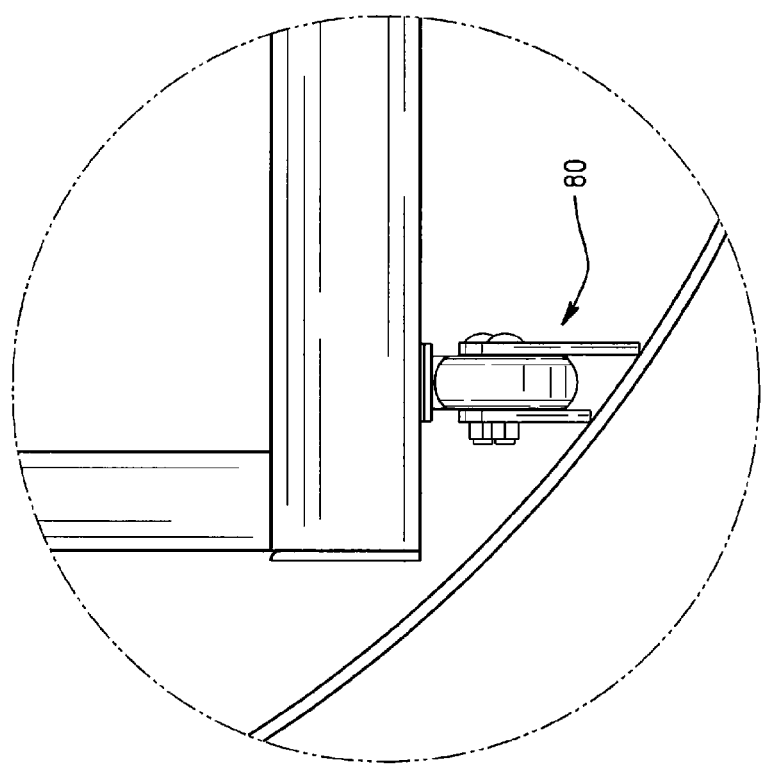
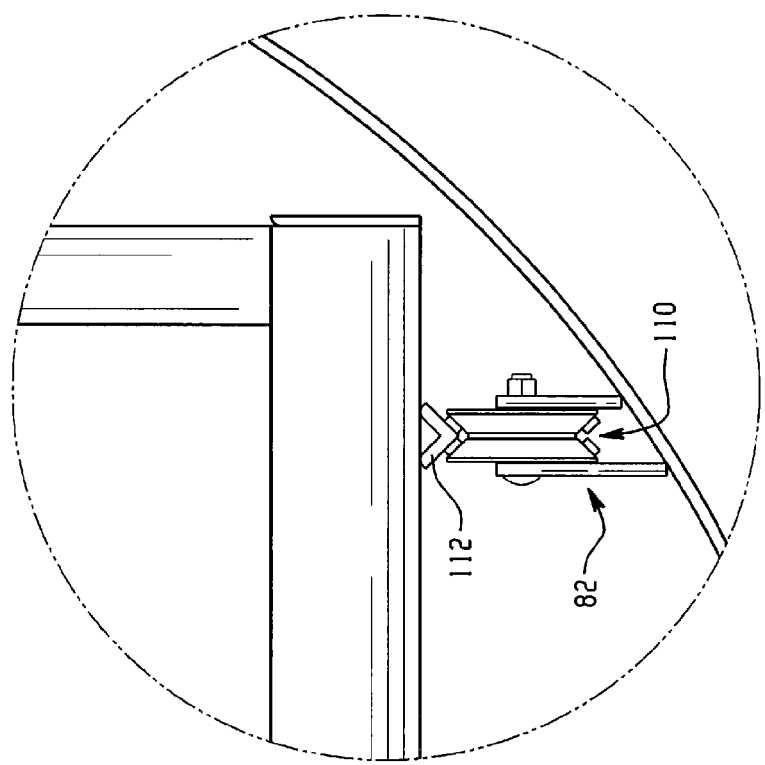
Fig. 15
Fig. 16

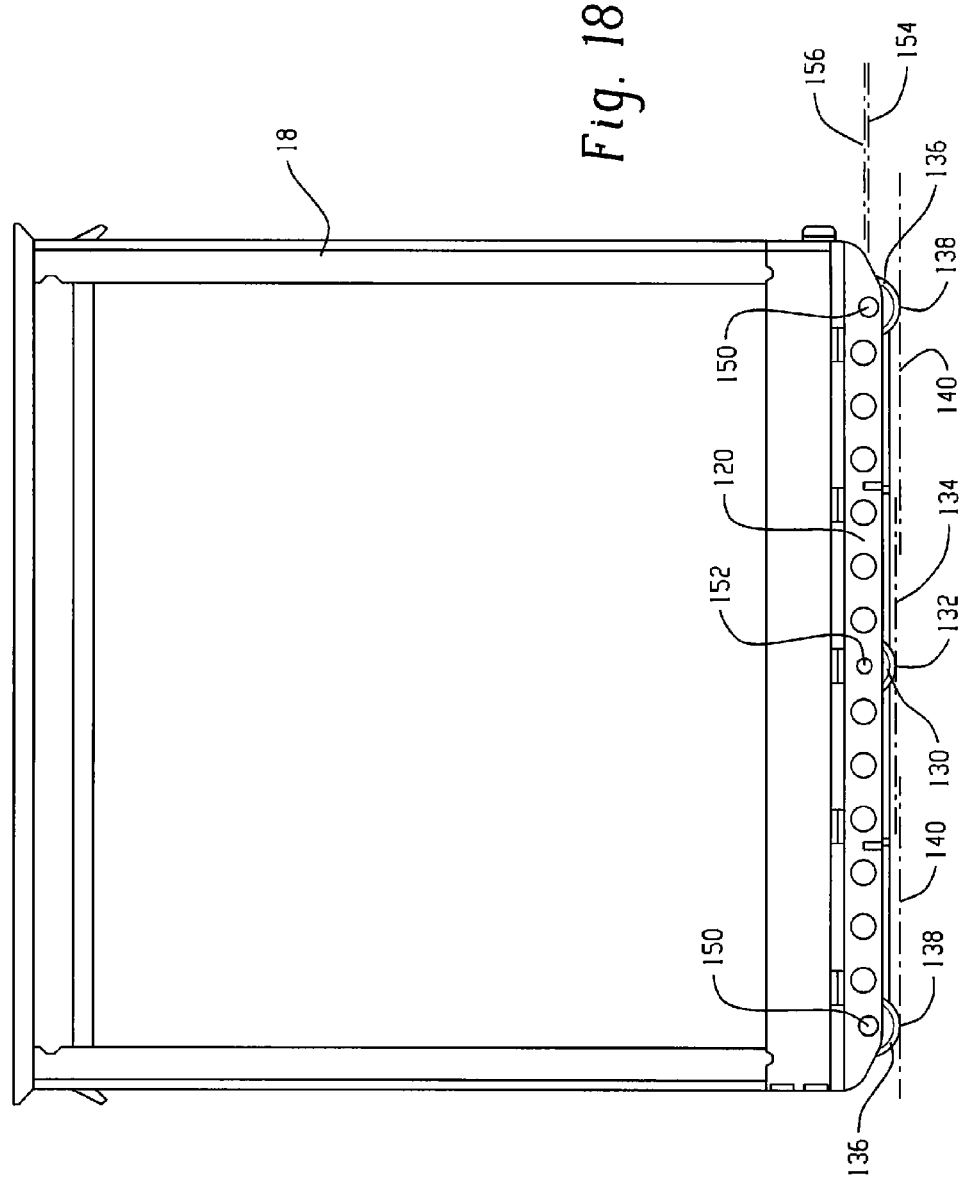

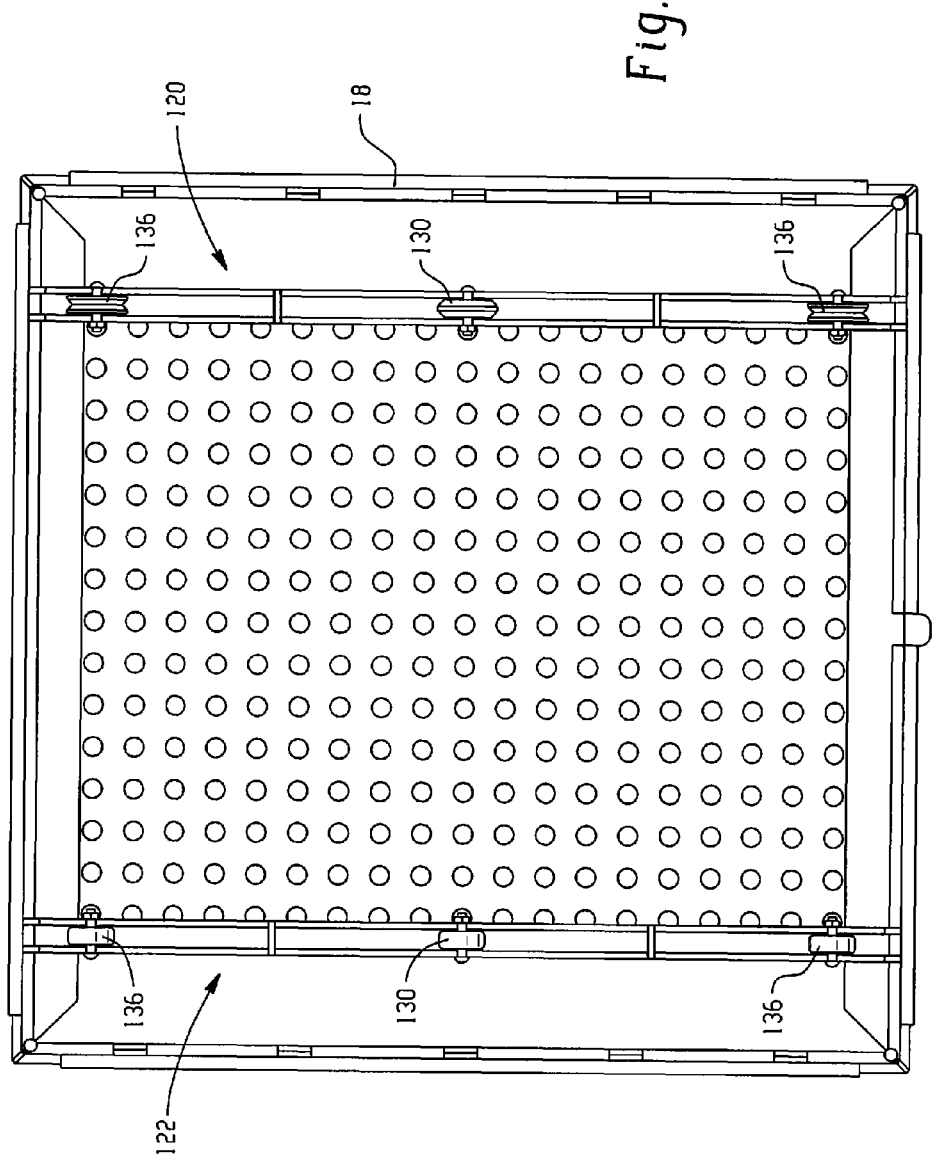

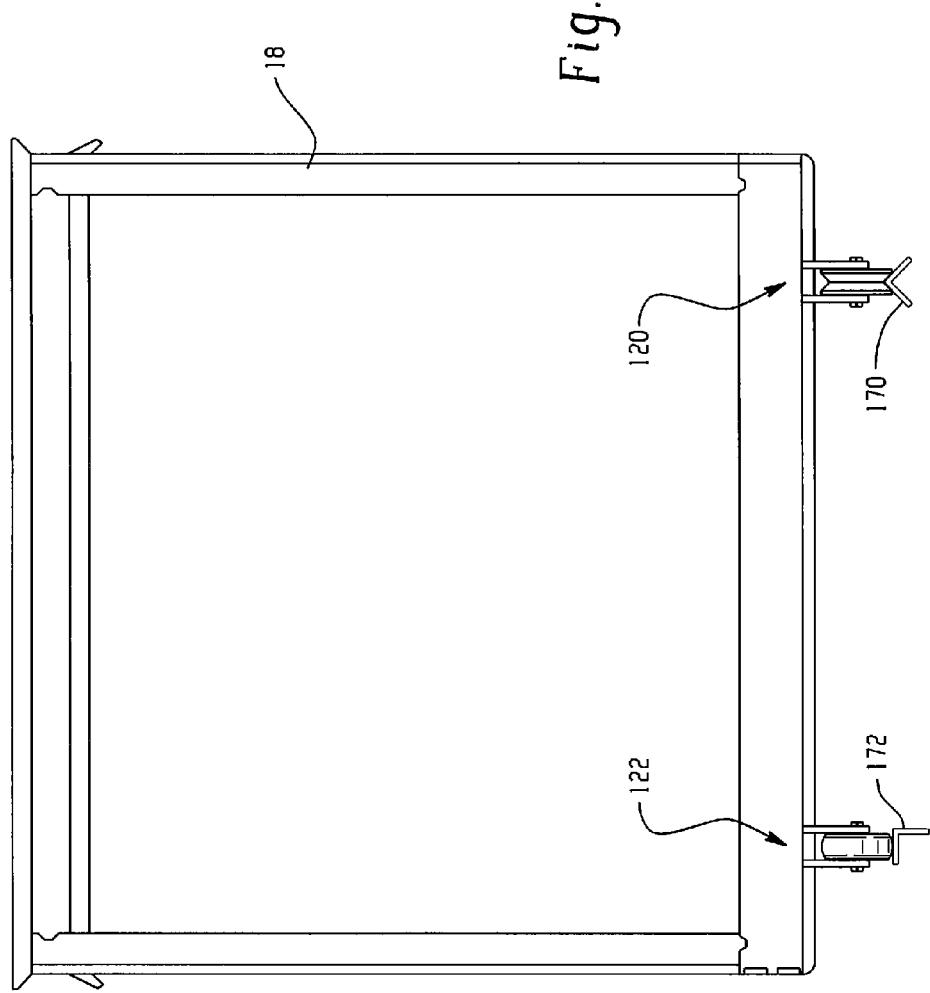

RETORT WITH PROGRESSIVE LATCH, ROLLER SUPPORT ARRANGEMENT AND METHOD AND SYSTEM FOR RECIPROCATION OF LOADS

CROSS-REFERENCE

This application claims the benefit of U.S. Provisional Application Ser. No. 61/522,052, filed Aug. 10, 2011.

TECHNICAL FIELD

The present application relates to devices for use in sterilization autoclaves (known in the industry as retorts), and in particular to a system and method for securing and supporting a basket or series of baskets containing product securely within a retort of the type in which the basket or baskets are moved back and forth during the sterilization process.

BACKGROUND

To sterilize many foods, pharmaceuticals and other products, to make them "shelf-stable," the products are subjected to a sterilization method by heating the food in its sealed container to a predetermined temperature. The product is held at this temperature for a product specific duration. This process is commonly referred to as an autoclave process, retort process or a sterilization process.

It is known to reciprocate product back and forth within the retort during the sterilization process by actually moving part of the internal retort structure that supports and secures the product baskets. In retorts in which multiple product baskets are loaded into the retort end to end along a reciprocating axis of the retort, it can be difficult to remove all slack, gaps or play between the product baskets prior to closing the retort door and beginning the retort process. When the reciprocating process begins the momentum of the product baskets tends to cause the product baskets to become more tightly compacted against each other in the reciprocating direction, creating the potential for gaps to form at opposite ends of the basket set between the basket set and the basket holding structure. These gaps form at the end of each stroke of reciprocation and can create an undesired level of force and vibration when the basket set shifts relative to the internal retort structure that is also moving. Specifically, the moving mass of the product baskets can be caused to slam against end located stop structure at the end of each stroke. Because the basket loads tend to be quite large, the impact created can be quite large. Supporting the baskets on roller supports during such movement while at the same time preventing lateral shifting of the baskets can also be difficult.

Accordingly, what is needed is a mechanism that can help eliminate gaps created by the reciprocating process. It would also be advantageous to provide a roller support system particularly adapted to improve loading, unloading and reciprocation of multiple basket loads.

SUMMARY

In one aspect, a retort includes a vessel having an access door and a basket supporting assembly within the vessel for supporting product baskets within the vessel, the basket supporting assembly movable back and forth within the vessel along a reciprocating path, the basket support assembly including a stop toward a first end of the assembly for limiting movement of product baskets toward the first end, the basket support assembly further including a latch mechanism toward a second end of the assembly for securing product baskets. The latch mechanism includes a latching part that is movable between a non-latching orientation and a latching orientation and an actuator. The actuator is operable to (i) move the latching part from the non-latching orientation to the latching orientation and (ii) maintain a bias of the latching part toward the latching orientation such that when a set of product baskets engaged by the latching part moves toward the first end of the vessel as a result of a reciprocating operation, the latching part moves under the bias of the actuator to remain in engagement with the set of product baskets and progressively reduce a spacing between the latching part and the stop as the set of product baskets shifts into a more compact arrangement during the reciprocating operation.

In the foregoing aspect, the actuator may operate to maintain a reduced spacing between the latching part and the stop during subsequent reciprocation.

In the foregoing aspect, the latching part may be pivotally mounted to the basket support assembly and include a basket engaging surface portion that is angularly offset from both horizontal and vertical when in the latching orientation.

The actuator may be formed by at least one bladder the effects pivotal movement of the latching part.

In another aspect, a retort includes a vessel having an access door and a frame situated within the vessel for moving a set of product baskets within the vessel, the frame including a stop toward a first end of the vessel for abutting against one end of the set of product baskets within the vessel, the frame further including a latch mechanism toward a second end of the vessel for securing product baskets on the frame. A drive mechanism is provided for reciprocating the frame back and forth in a reciprocating path that runs lengthwise from a location toward the first end of the vessel to a location toward the second end of the vessel. The latch mechanism includes a latching part that is movable between a non-latching orientation and a latching orientation and an actuator that operates to (i) move the latching part from the non-latching orientation to the latching orientation and (ii) maintain a bias of the latching part toward the latching orientation such that when a product basket engaged by the latching part moves toward the first end of the vessel as a result of a reciprocating operation, the latching part moves under the bias of the actuator to remain in engagement with the product basket and progressively reduce a spacing between the latching part and the stop as the set of product baskets shifts into a more compact arrangement during the reciprocating operation.

In the foregoing aspect, the latching part is pivotally mounted to the frame and includes a basket engaging surface portion for contacting an edge of the product basket when the latching part is in the latching orientation, the surface portion offset angularly from both first and second planes that define the edge of the product basket, where the first and second planes are perpendicular to each other and the surface portion is not parallel to either of the first and second planes.

The latch mechanism may include a first plate connected for movement with the latching part and a second plate connected for movement with the latching part, the second plate spaced apart from the first plate, and the actuator may be formed by a first bladder, a second bladder, and an intermediate plate between the first and second bladder, the intermediate plate connected to the frame and extending between the first plate and the second plate, the first bladder located between the first plate and the intermediate plate, the second bladder located between the intermediate plate and the second plate. When the first bladder is expanded and the second bladder is collapsed, the first bladder causes a spacing between the intermediate plate and the first plate to enlarge and a spacing between the intermediate plate and the second plate to reduce such that the latching part moves to the latching orientation. When the first bladder is collapsed and the second bladder is expanded, the second bladder causes the spacing between the intermediate plate and the second plate to enlarge and the spacing between the intermediate plate and the first plate to reduce such that the latching mechanism moves to the non-latching orientation.

The intermediate plate may be pivotally connected to the frame at one end and has a free end that moves, a pivot axis of the intermediate plate is spaced apart from a pivot axis of the latching part along the reciprocating path and the free end of the intermediate plate is located between the pivot axis of the latching part and the pivot axis of the intermediate plate. The first plate may be rigidly connected to the latching part, and the second plate may be rigidly connected to the latching part.

The frame may include first and second spaced apart rail members, with the latching part formed by a first latching bracket and a second latching bracket positioned between the first and second spaced apart rail members, where the first plate connects the first latching bracket and the second latching bracket, the second plate connects the first latching bracket and the second latching bracket, and the intermediate plate is positioned between the first and second spaced apart rail members.

The actuator may include a first fluid path for controllably expanding and collapsing the first bladder and a second fluid path for controllably expanding and collapsing the second bladder. At least one source of pressurized air may be associated with each of the first fluid path and the second fluid path.

When the latching part is in the latching orientation the basket engaging surface may be raised above spaced apart first and second rails of the frame for engaging a bottom corner edge of the product basket, and when the latching part is in the non-latching orientation the basket engaging surface may be lowered into a space between the first and second rails.

In a further aspect, a retort basket support assembly for supporting a retort basket during both transfer and reciprocating processing of the retort basket is provided. The assembly includes a roller arrangement, wherein the roller arrangement includes a plurality of transfer rollers having external surfaces that define a first horizontal plane, and a plurality of support rollers having external surfaces that define a second horizontal plane that is offset from the first horizontal plane.

In the foregoing aspect, each transport roller may be located between two support rollers to help support a product basket during loading and unloading.

The plurality of support rollers and the plurality of transfer rollers may be arranged in first and second spaced apart rail assemblies to define a first line of rollers and a second line of rollers that is spaced apart from and runs parallel to the first line of rollers, the first line of rollers including both support rollers and transfer rollers and the second line of rollers including both support rollers and transfer rollers.

Support rollers of the first line of rollers and the second line of rollers may be laterally paired with each other and transfer rollers of the first line of rollers and the second line of rollers may be laterally paired with each other.

In one implementation, the first rail assembly and second rail assembly are both mounted to a bottom of a retort basket structure such that the support rollers and transport rollers face downwardly from the retort basket structure and the second horizontal plane is lower than the first horizontal plane.

In another implementation, the first rail assembly and second rail assembly are both mounted within a retort vessel having an access door and a frame situated within the vessel for moving product baskets back and forth within the vessel, the frame defining a basket load zone, the first rail assembly and second rail assembly oriented such that the support rollers and transport rollers face upwardly and the second horizontal plane is higher than the first horizontal plane.

In one implementation, the support rollers have a diameter that is the same as a diameter of the transfer rollers, the support rollers mounted on respective rotation axes that lie in a third plane and the transfer rollers mounted on respective rotation axes that lie in a fourth plane that is offset from and parallel to the third plane.

In another implementation, the support rollers have a diameter that is different than a diameter of the transfer rollers, the support rollers and the transfer rollers having respective rotation axes that lie in a common plane.

In still another aspect, a retort includes a vessel having an access door and a frame situated within the vessel for moving a set of product baskets within the vessel, the frame defining a basket load zone for a plurality of product baskets. A support arrangement is provided for supporting the product baskets within the vessel during movement of the frame, the support arrangement extending in a lengthwise direction of the vessel from a location toward a first end of the vessel to a location toward a second end of the vessel. A drive mechanism is provided for reciprocating the frame back and forth in a reciprocating path that extends from the first end toward the second end of the vessel, the drive mechanism operates to reciprocate the frame at between 60 and 95 strokes per minute, where the stroke length is between about four inches and about eight inches.

In one implementation, the stroke length is between about five inches and about seven inches.

In another implementation, the stroke length is about six inches.

In one implementation, the drive mechanism operates to reciprocate the frame at between 80 and 95 strokes per minute.

In yet a further aspect, a method of processing product in a retort involves: reciprocating the food product containers back and forth within a retort vessel at between 60 and 95 strokes per minute, where the stroke length is between about four inches and about eight inches; and during reciprocation, spraying heated water and/or steam onto the food product containers. A cooling spray may also later be provided.

The reciprocating step may be carried out at between 80 and 95 strokes per minute and the stroke length is between about five inches and about seven inches.

BRIEF DESCRIPTION OF THE DRAWINGS

FIGS. 8-11 show one embodiment of a roller arrangement within a retort vessel;

FIGS. 12-16 show another embodiment of a roller arrangement within a retort vessel; and FIGS. 17-20 show an embodiment in which the rollers are located on the bottom of the retort basket structure.

DETAILED DESCRIPTION

Figure 1:
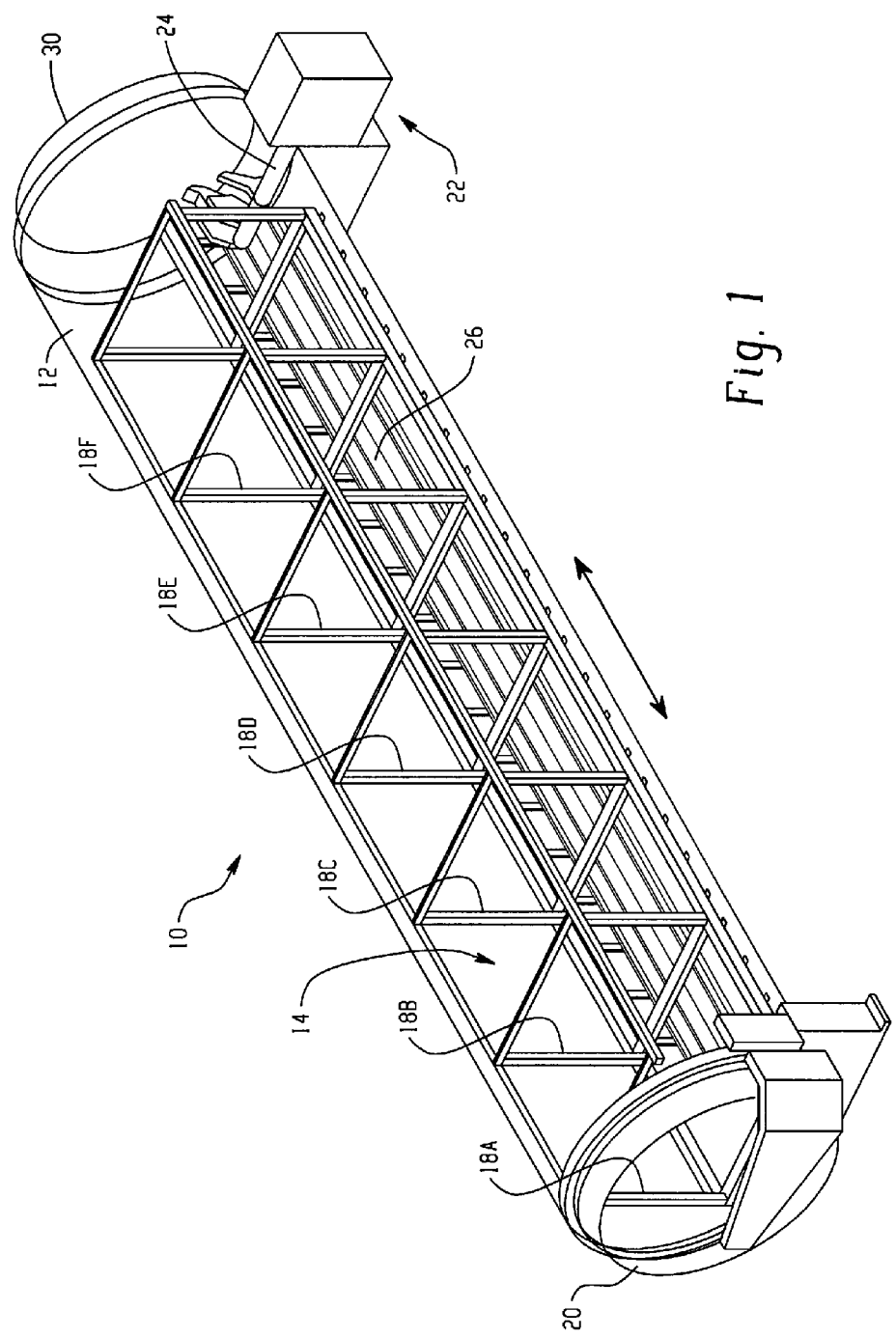
FIG. 1. is a perspective view of a retort vessel.

Referring to FIG. 1, an apparatus 10 (e.g., an autoclave or retort used for cooking and/or sterilization) includes a vessel 12 that defines a basket receiving volume 14 into which a set of baskets 18 are inserted in an end to end arrangement. In FIG. 1 the vessel is shown as transparent, but would typically be of metal construction. The size of the vessel may vary widely. In the illustrated embodiment each basket 18 is represented by a box-shaped frame structure. Each basket would typically be loaded with multiple product containers (not shown), which may take the form of cans, jars, pouches or any other suitable product package. The containers may include foods, pharmaceuticals or other products that are to be heated within their sealed containers for sterilization and/or cooking.

The vessel 12 includes a hinged door 20 at one end for loading and unloading of the baskets. Generally, the baskets 18 including product containers are loaded via an automated shuttle or the like, which urges the baskets into the basket receiving volume 14, then, after processing, retrieves same. As described in greater detail below, rollers may be provided along a lower part of the basket receiving volume 14, or on the baskets themselves, to support and guide the baskets 18 on their ingress and egress into and out of the vessel, and a frame structure 26, or other basket support assembly, may be located within the vessel for moving the baskets back and forth during the retort process. The frame structure is driven in a reciprocating manner by a motor and drive arrangement 22 that has an associated drive shaft assembly 24 that extends through a wall of the vessel and is operatively couple to the frame. The reciprocating path runs lengthwise from a location toward the door end of the vessel to a location toward the far end 30 of the vessel.

In one implementation, the drive for reciprocating the frame back and forth in the reciprocating path (e.g., in a forward stroke, followed by a backward stroke etc.) operates to reciprocate the frame at between 60 and 95 strokes per minute, where the stroke length is between about four inches and about eight inches (e.g., between about five inches and about seven inches (e.g., about six inches)). The drive mechanism may operate to reciprocate the frame at between 80 and 95 strokes per minute. Such a reciprocation rate has been found to reduce the required heating time of the retort process without excessively agitating the product in the containers. However, in other embodiments and for certain products, the reciprocating rate may be taken higher, such as in the range of about 60 to 300 strokes (e.g., 60 to 200 strokes).

Figure 2:
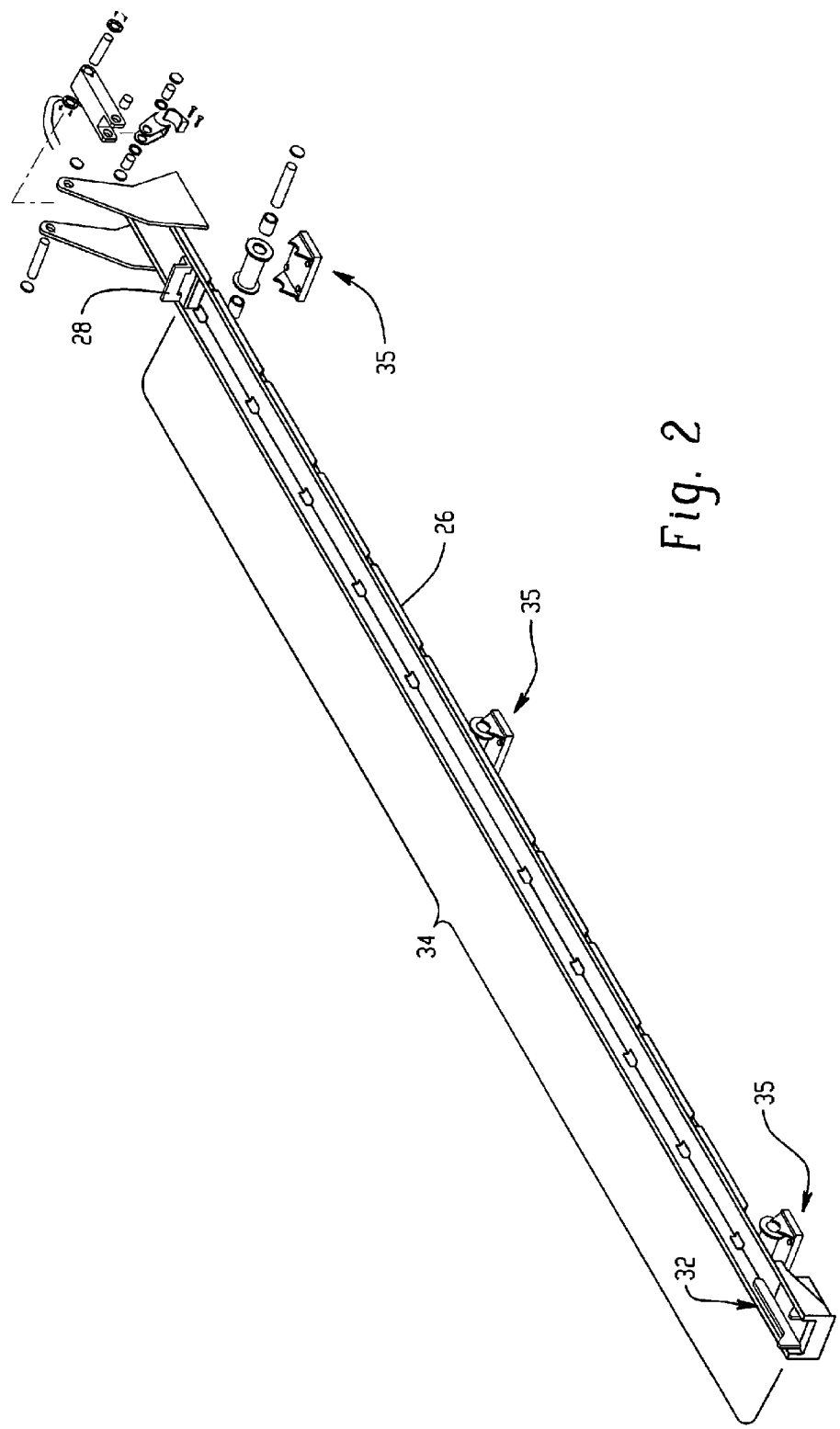
FIG. 2 is a perspective view of a retort vessel frame arrangement.

Referring now to FIG. 2, the frame 26 is shown and includes a stop 28 toward the far end 30 of the vessel for abutting against one end of the set of product baskets within the vessel, and the frame further includes a latch mechanism 32 toward a door end of the vessel for securing the set of product baskets on the frame. Thus, the frame defines a basket load zone 34 for a plurality of product baskets, the load zone extending lengthwise along the vessel. The frame may be supported on a set of spaced apart idler rollers 35 that are mounted within the vessel.

The latch mechanism 32 and stop 28 cooperate to secure the baskets for movement with the frame 26 during reciprocation of the frame. In this regard, referring again to FIG. 1, end basket 18F would engage with the stop 28 and end basket 18A would engage with the latch. The operation of the latch mechanism is described below with respect to FIGS. 3-7, where each figure designated "A" corresponds to the latch mechanism when in a non-latching orientation and each figure designated "B" corresponds to the latch mechanism when in a latching orientation.

Figure 3A:
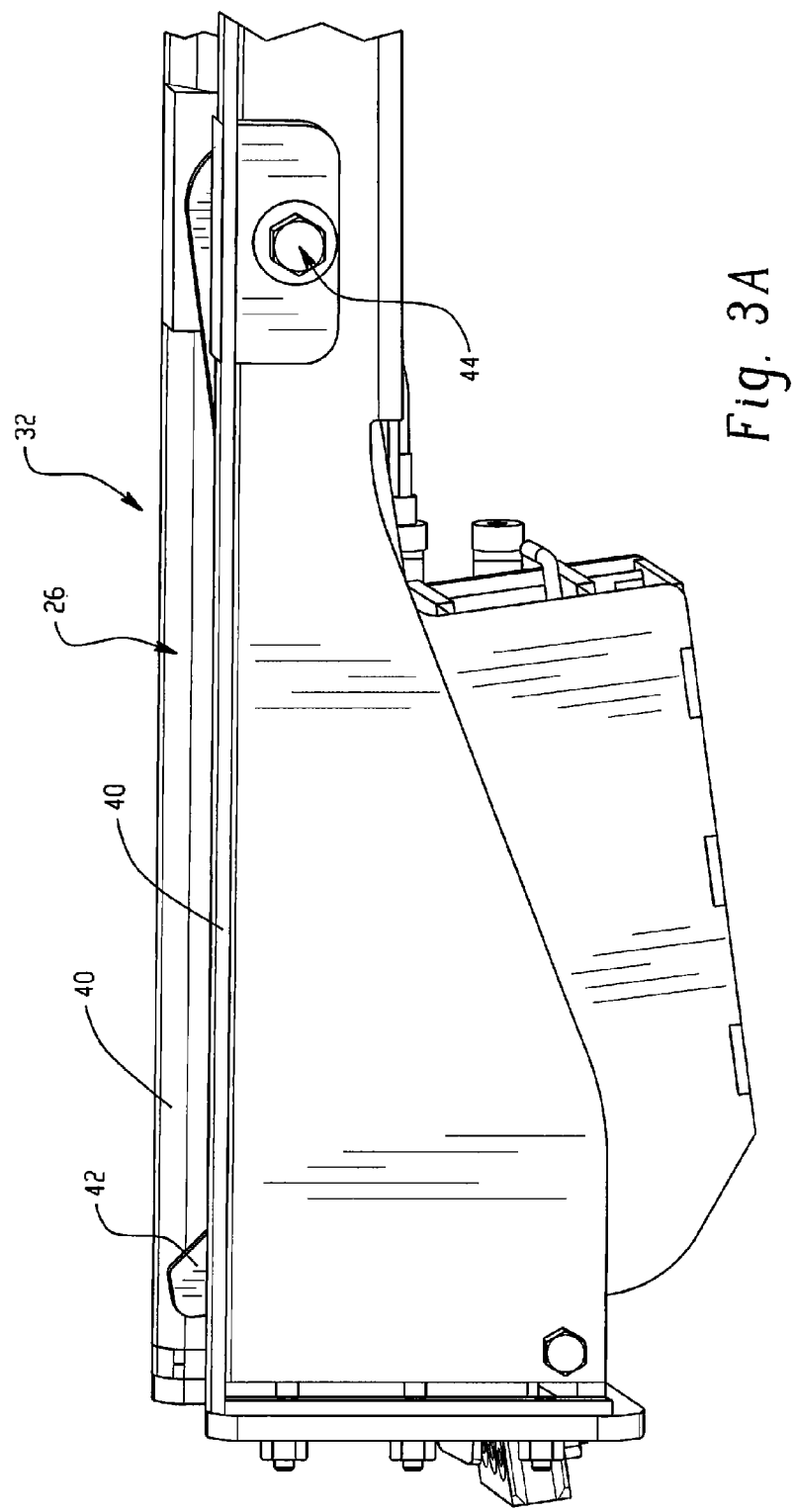
FIGS. 3-7 illustrate a latching mechanism associated with one end of the frame of FIG. 2.
Figure 4A:
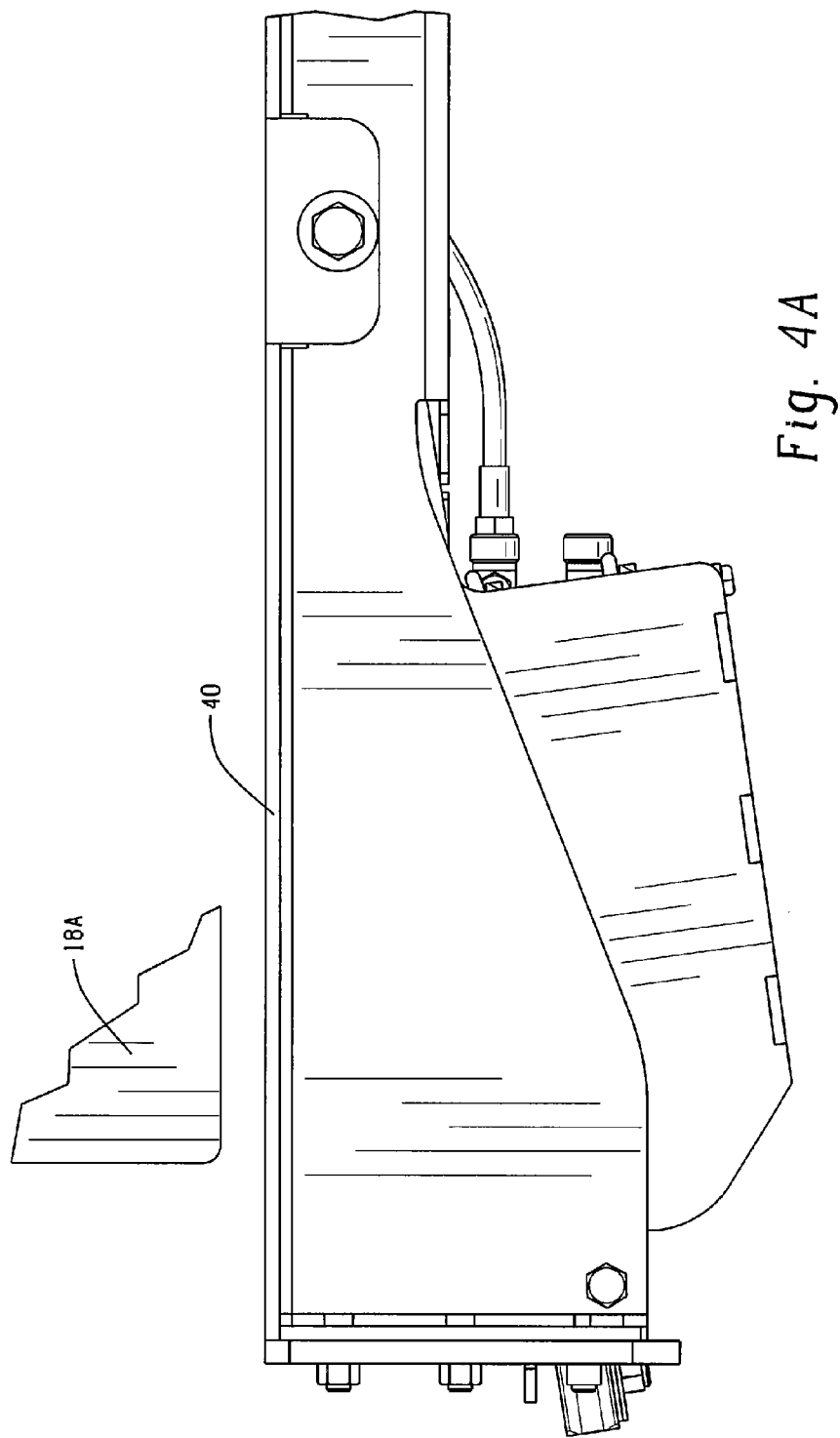
Figure 4B:
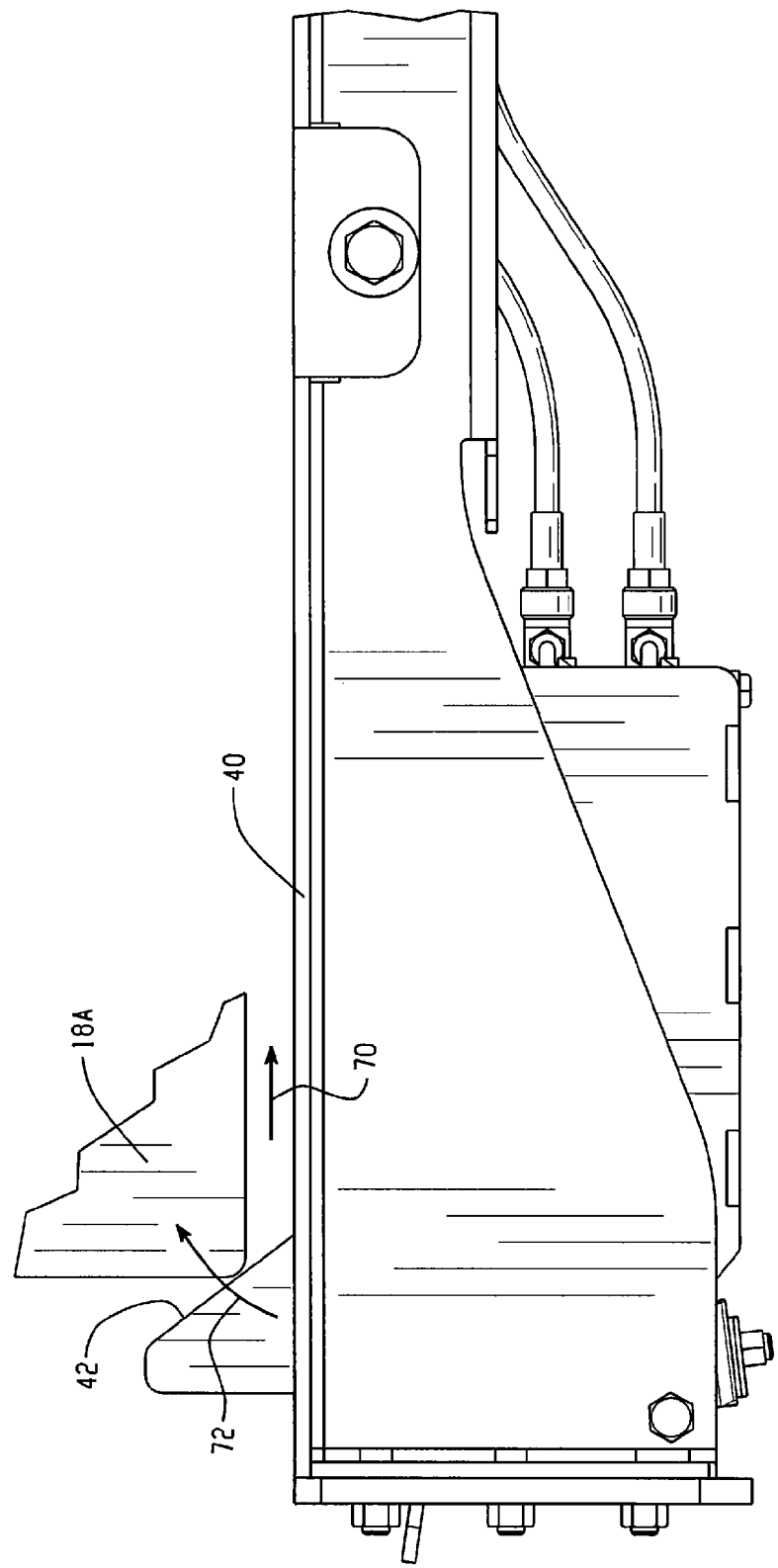

As seen in FIGS. 3A and 3B, the illustrated latch mechanism is disposed within a space defined by two spaced apart rails 40 of the frame 26. In the non-latching orientation of FIG. 3A, latch engaging surfaces 42 of the latch mechanism are recessed below the top surfaces of the rails 40. In the latching orientation of FIG. 3B, latch engaging surfaces 42 of the latch mechanism are raised above the top surfaces of the rails. A pivotal connection 44 to the rails 40 enables the latch mechanism to move between the two orientations. As seen in FIGS. 4A and 4B, the baskets (represented by the lower corner of basket 18A) are supported above the rails 40 such that the lower edge of the baskets are free to move past the latch mechanism when it is in the non-latching orientation, while the basket engaging surfaces 42 of the latch engaging surfaces 42 are raised high enough to engage the lower corner or edge of the baskets when the latch mechanism is in the latching orientation.

Figure 5B:
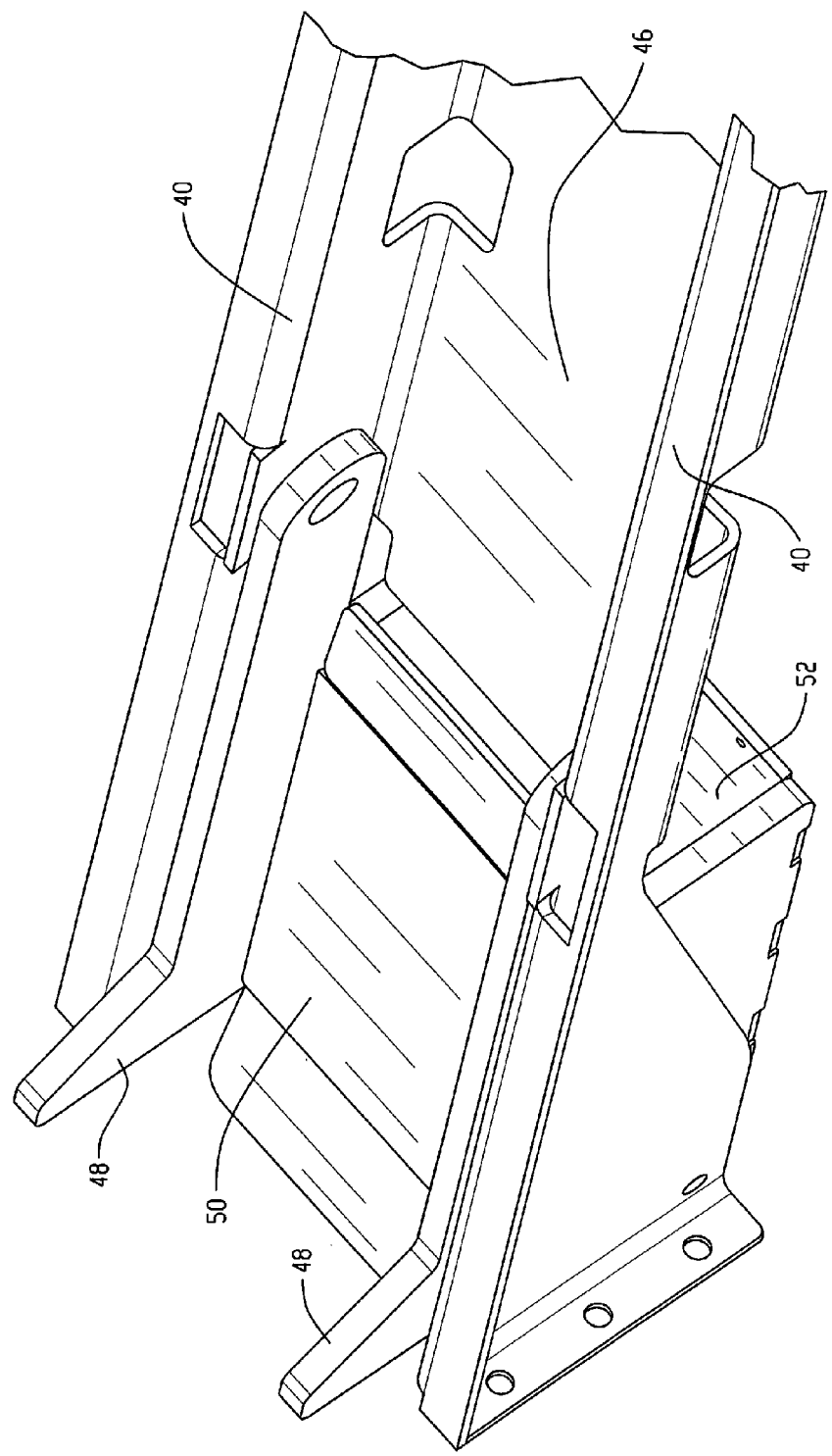

Referring to FIGS. 5A and 5B, the frame rails 40 are connected by a lateral plate 46 and a latching part of the latching mechanism is formed by a first latching bracket 48 and a second latching bracket 48, both positioned between the first and second spaced apart rails 40. An upper laterally extending plate 50 connects the two latching brackets 48 and a lower laterally extending plate 52 connects the two latching brackets 48.

Figure 6A:
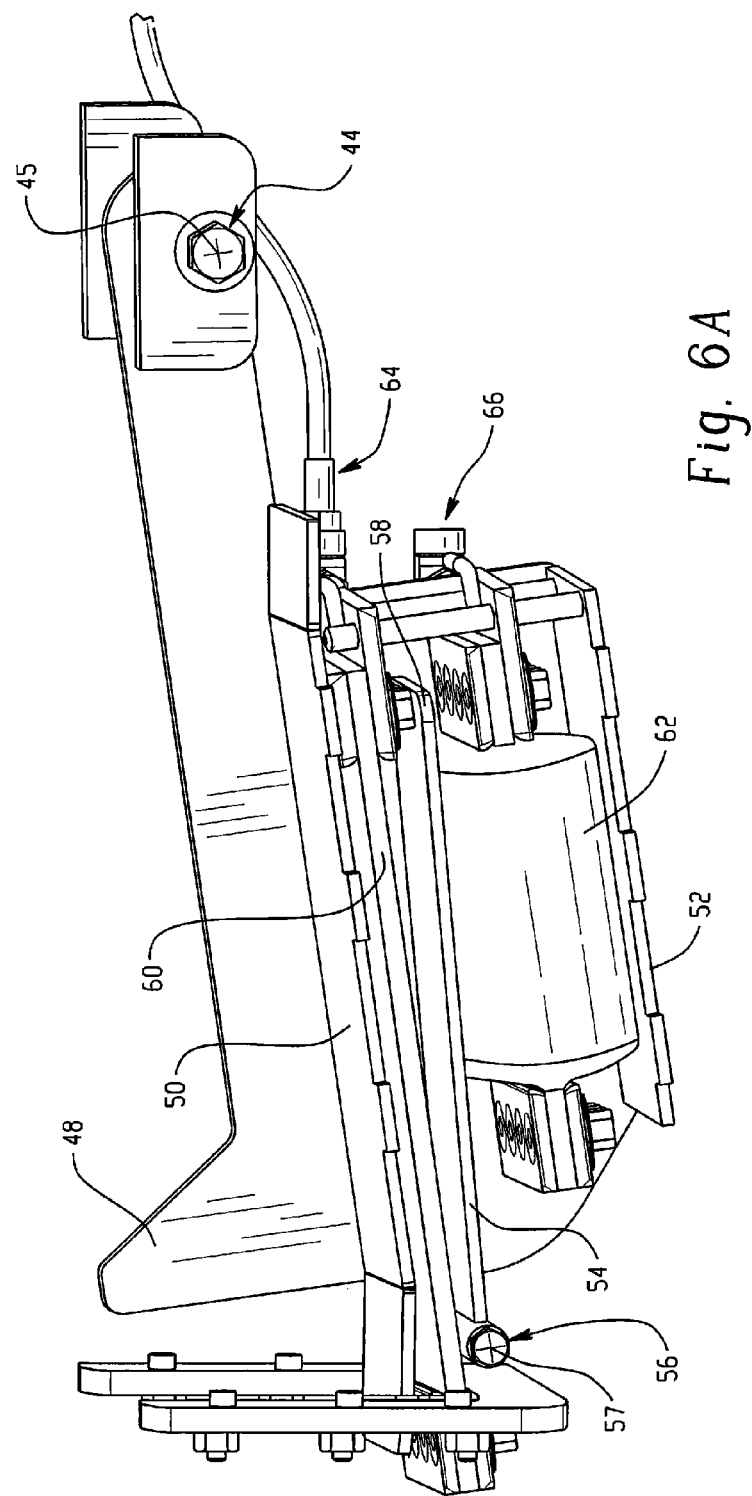
Figure 6B:
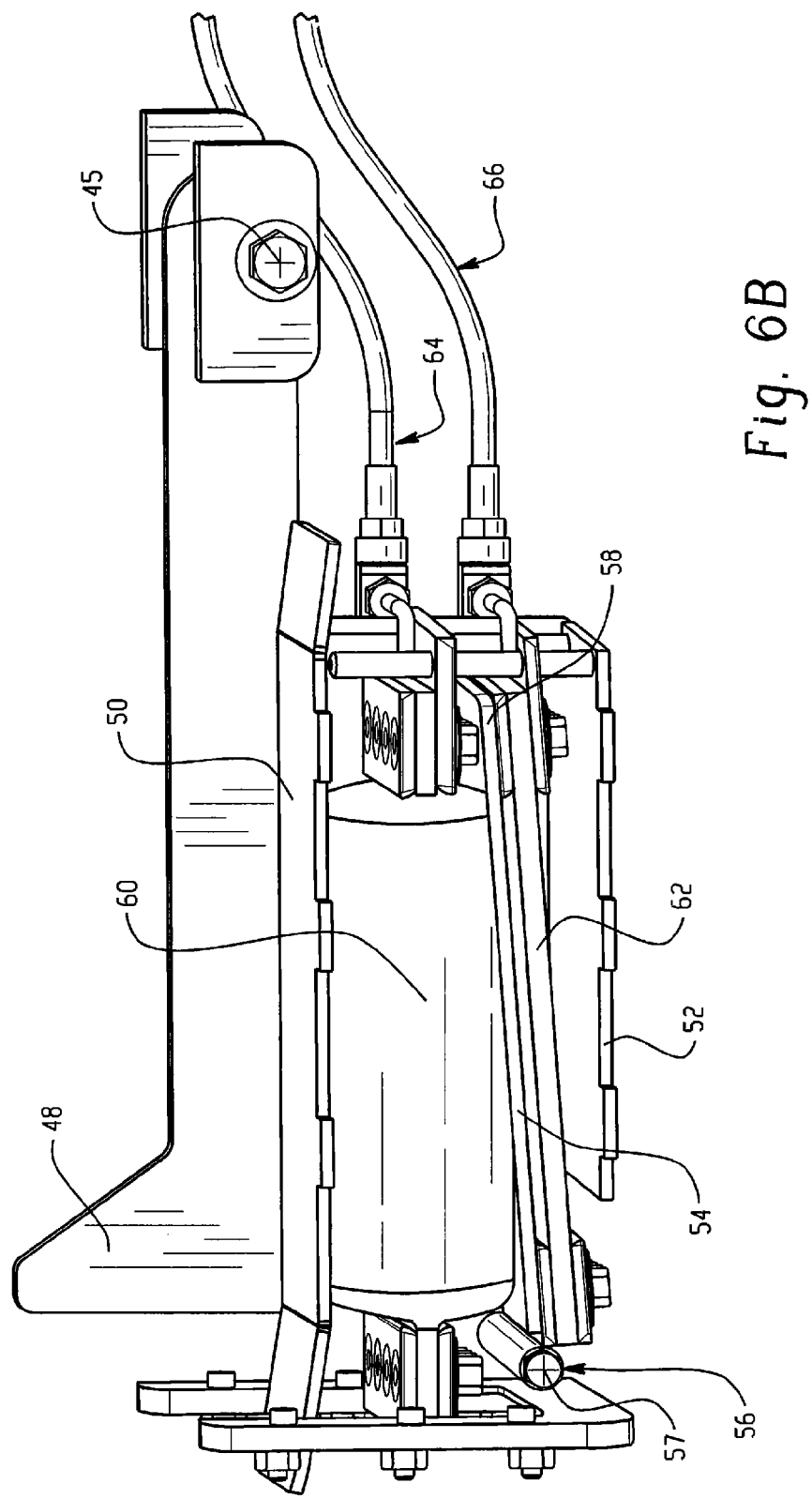

In the views of FIGS. 6A and 6B the frame rails 40 and plate 46 and one latching bracket 48 have been removed for the purpose of explaining the operation of the latch mechanism and, in particular, the actuator for the latch mechanism. As shown, an intermediate plate 54 is located between the upper plate 50 and lower plate 52. The intermediate plate 54 is pivotally connected at one end to the frame (not shown) via a pivotal connection 56 and has a free end 58 that moves. The pivot axis 57 of the intermediate plate 54 is spaced apart from the pivot axis 45 of the latching mechanism along the reciprocating path and the free end 58 of the intermediate plate 54 is located between the pivot axis 45 and the pivot axis 57. The upper and lower plates 50 and 52 are rigidly connected to the latching brackets 48.

The illustrated actuator includes an upper bladder 60 and a lower bladder 62, with the intermediate plate 54 located between the two bladders 60 and 62. The intermediate plate extends from the pivotal connection into to the space between the plates 50 and 52. Upper bladder 60 is located between the upper plate 50 and the intermediate plate 54, and the lower bladder 62 is located between the intermediate plate 54 and the lower plate 52. When the upper bladder 60 is expanded and the lower bladder 62 is collapsed (per FIG. 6B), the upper bladder 60 causes a spacing between the intermediate plate 54 and the upper plate 50 to enlarge and a spacing between the intermediate plate 54 and the lower plate 52 to reduce such that the latching brackets pivot upward to the latching orientation. When the upper bladder 60 is collapsed and the lower bladder 62 is expanded, the lower bladder causes the spacing between the intermediate plate 54 and the lower plate 50 to enlarge and the spacing between the intermediate plate 54 and the upper plate 50 to reduce such that the latching brackets 48 pivot downward to the non-latching orientation.

Each bladder includes a respective fluid path 64, 66 for controllably expanding and collapsing the respective bladder. A source of pressurized air (e.g., a source of 40 to 80 psi (e.g., 50 to 70 psi)) may be associated with each of the fluid paths via controllable valves for allowing pressurized air to flow to the bladder. Controllable air release valves may also be provided in association with the fluid paths for permitting bladder collapse. The bladders may be formed of a tubular-shape material such as silicone, with the ends of the tubular shape clamped as shown.

Figure 7A:
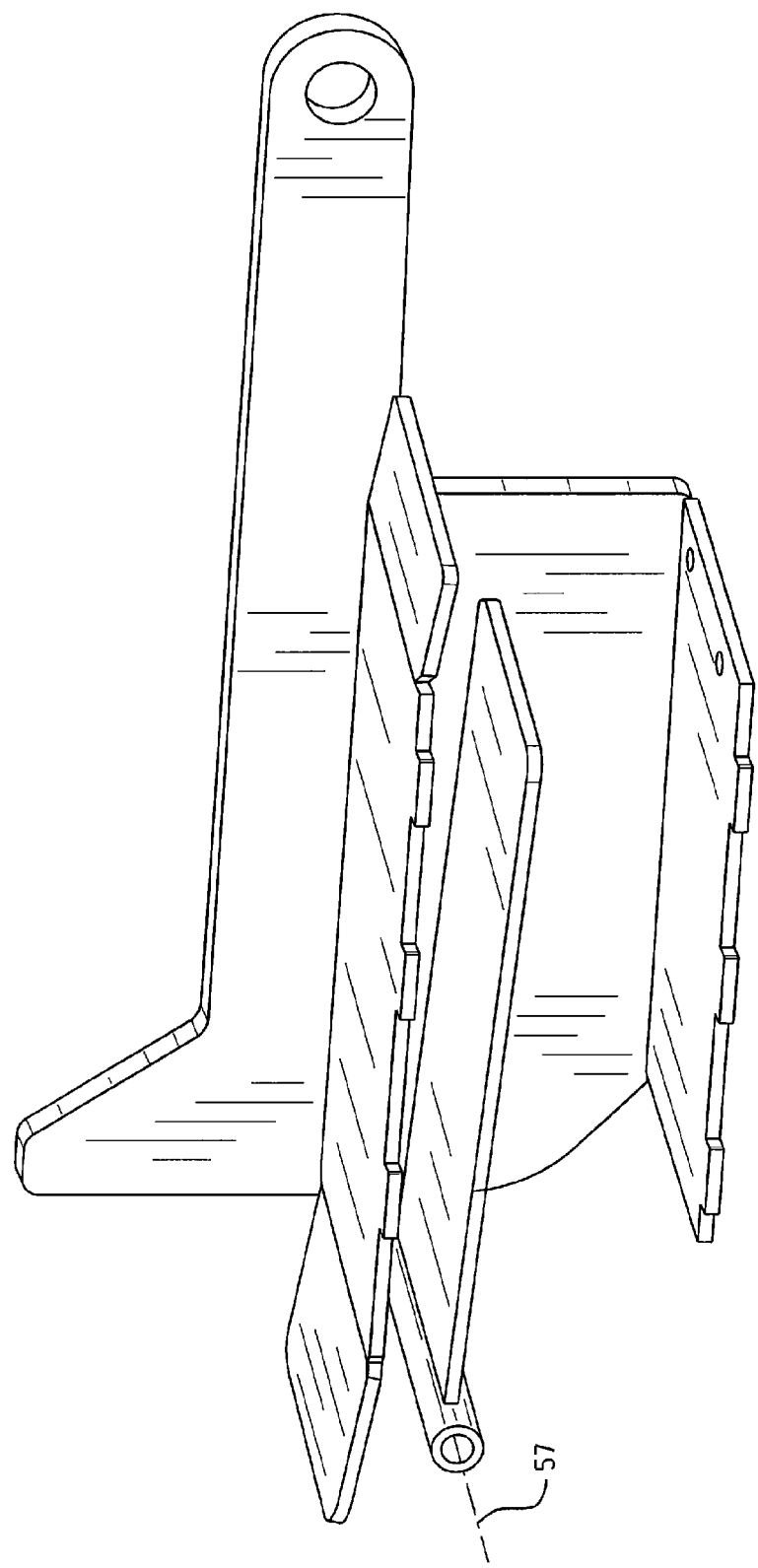
Figure 7B:
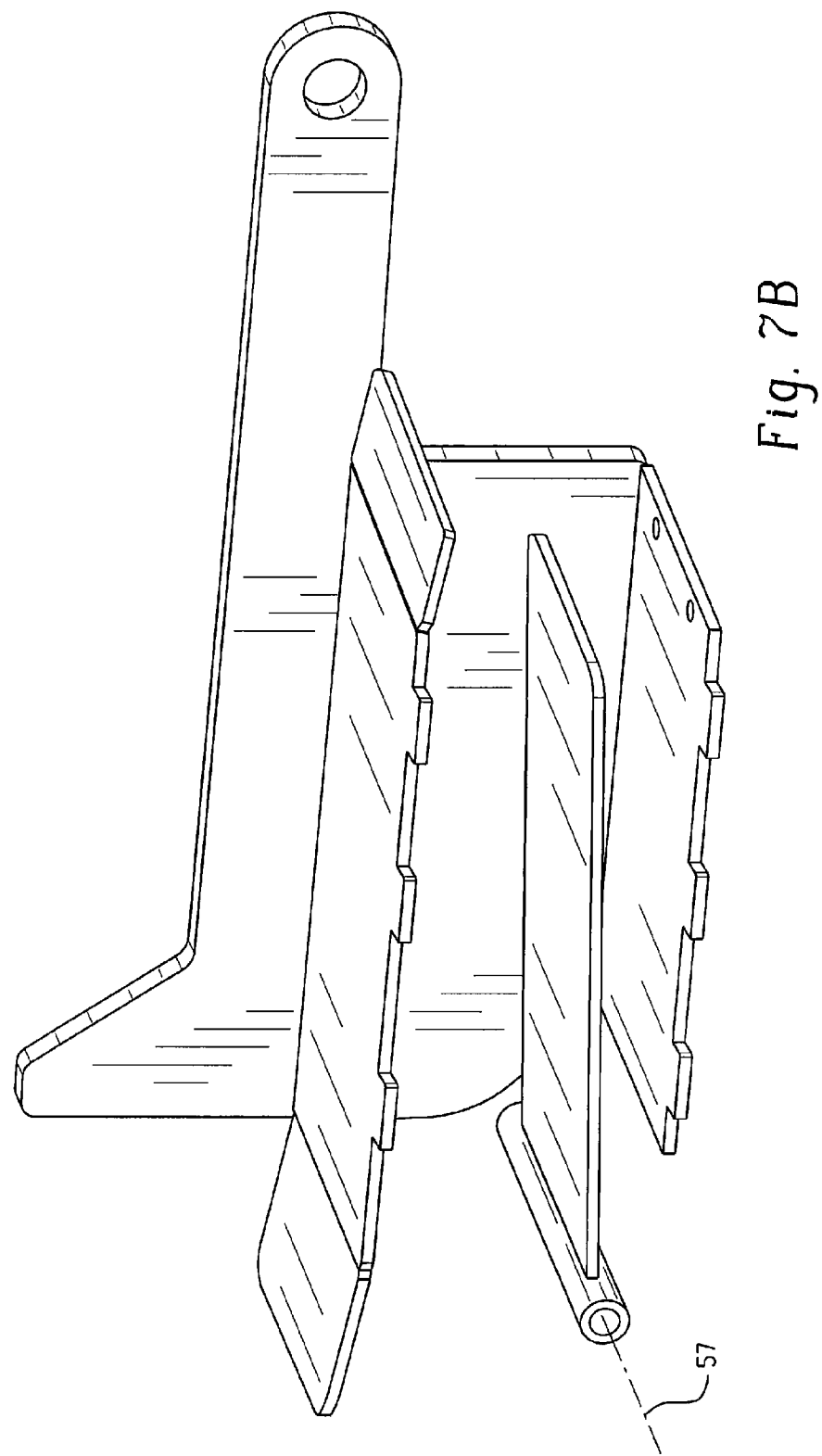

FIGS. 7A and 7B show views with bladders removed. Note that pivot axis 57 of intermediate plate 54 is fixed and does not shift vertically or horizontally (relative to the frame) when the latching mechanism is moved between the two orientations.

Referring again to FIGS. 4A and 4B, in operation the actuator operates to move the latching brackets from the non-latching orientation of FIG. 4A to the latching orientation of FIG. 4B after the load zone 34 (FIG. 2) has been fully loaded with baskets. The actuator maintains a bias force (via the pressurization of the upper bladder) of the latching brackets upward toward the latching orientation such that when a product basket 18A that is engaged by the latching surfaces 42 moves toward the far end of the vessel (e.g., to the right in FIG. 4B as shown by arrow 70) as a result of a reciprocating operation, the latching brackets move under the bias of the actuator (e.g., in the pivotal direction shown by arrow 72) to keep the surfaces 42 in engagement with the product basket 18A and progressively reduce a spacing between the latching surfaces 42 and the stop 28 (FIG. 2) as the set of product baskets shifts into a more compact arrangement during the reciprocating operation. Thus, the baskets can move into a further and further compact arrangement during reciprocation (within limits of the basket dimensions) and the latching mechanism will likewise progressively move to eliminate any gap between the end basket 18A and the latching surfaces 42. Due to the continued pressurization of the bladder 60 during this process, additional air will be added to the bladder as it expands and will act to maintain the reduced spacing between latching surfaces 42 and stop 28 so that the more compact basket arrangement is also maintained during subsequent reciprocation of the baskets.

In alternative arrangements, other actuators may be used, such as, for example, (i) one or more fluidically controlled pistons to pivot the latching brackets, where one end of the piston is pivotally connected to the frame and the opposite end is pivotally connected to the latch, or (ii) one or more springs that are used to pivot the latching brackets upward, with an associated mechanical advantage arrangement that enables an operator to pivot the latching brackets downward into the non-latching orientation. Any of the bladder arrangement, the piston arrangement or the spring arrangement would operate as means to move the latching part from the non-latching orientation to the latching orientation and as a means to maintain a bias of the latching part toward the latching orientation such that when a product basket engaged by the latching part moves toward the far end of the vessel as a result of a reciprocating operation, the latching part moves under the bias of the actuator to remain in engagement with the product basket and progressively reduce a spacing between the latching part and the stop as the set of product baskets shifts into a more compact arrangement during the reciprocating operation.

Figure 8:
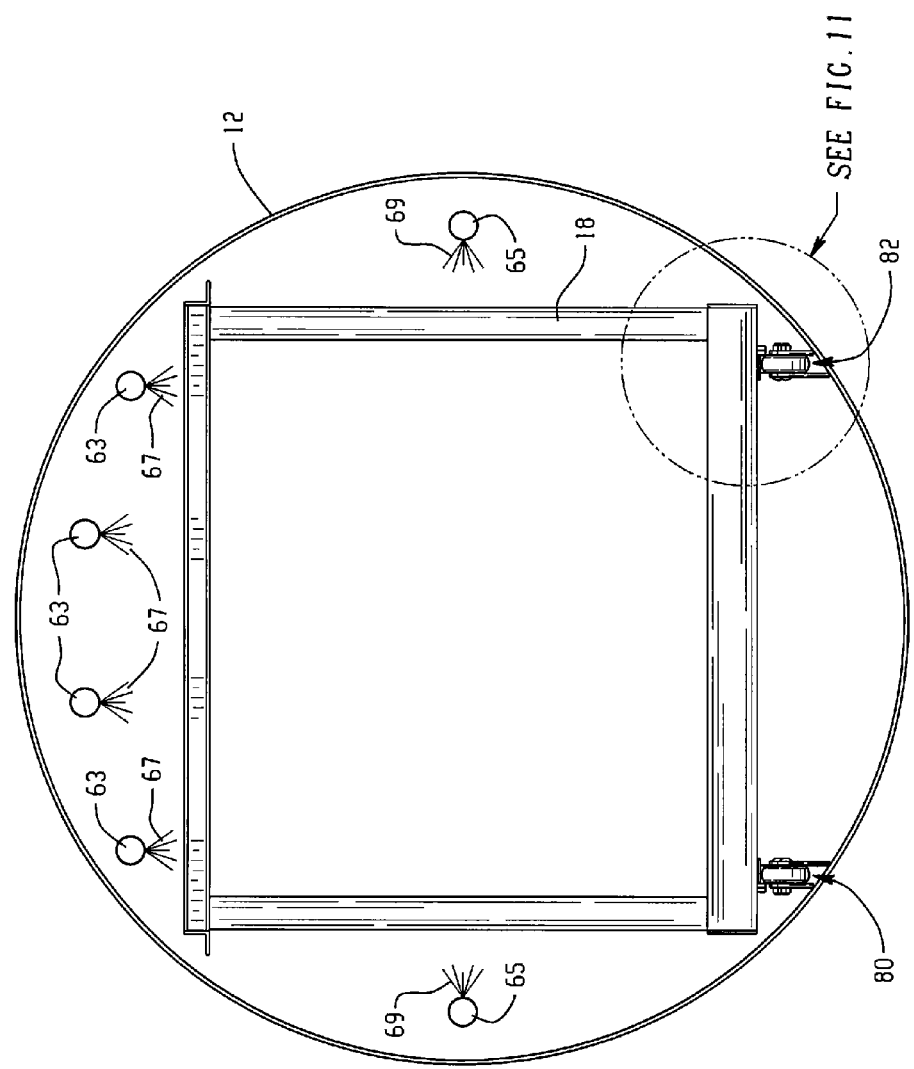
Figure 11:
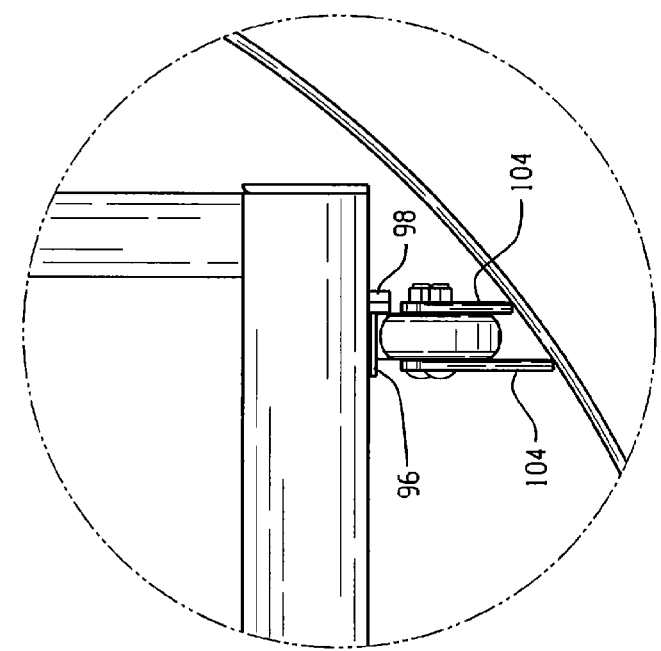

The above-described system may be used with any suitable retort heating system, such as steam heating, hot water spray heating, immersion heating, etc. Is some instances, it may be desirable to heat the product to temperatures above about 200° F., such as above about 220° F., such as above about 250° F., etc. In FIG. 8, an exemplary hot water spray system is shown by upper manifolds 63 and side manifolds 65 with associated sprays 67 and 69 from nozzles along the manifolds. More or less manifolds could be used depending upon the particular need. Steam and overpressure may also be used as is typical for water spray retorts. The manifolds could also be used for spraying cooling water during a subsequent cooling step of the process.

Referring now to FIGS. 8-11, one embodiment of a roller arrangement for supporting the product baskets within the vessel 12 during movement of the frame and for supporting the product baskets during loading and unloading of the vessel 12 is shown schematically. The roller arrangement includes two spaced apart lines 80 and 82 of rollers extending in a lengthwise direction of the vessel from a location toward a door end of the vessel to a location toward the far end of the vessel. The frame is not shown in FIGS. 8-11 for simplicity. The roller arrangement includes a plurality of transfer rollers 84 having outer product basket engaging surfaces 86 that define a horizontal plane 88 and a plurality of support rollers 90 having product basket engaging surfaces 92 that define a horizontal plane 94 that is raised above the horizontal plane 88. The distance between the two planes may, for example, be on the order of about 1/16 of an inch to 1/4 inch (e.g., about 1/8 inch). Multiple sets of support rollers 90 are located along the basket load zone and spaced such that when the basket load zone is full of product baskets each product basket will be supported only by support rollers 90 and not by any transfer rollers 84 (e.g., per FIG. 9). In the illustrated embodiment, each product basket will be supported by four support rollers 90 spaced apart to define corners of a square or rectangle, with each support roller located toward a respective lower corner of the product basket, but variations are possible. Multiple transport rollers 84 are located between the sets of support rollers 90 of each roller line to help support the product baskets during loading and unloading when the product baskets are not fully supported by the support rollers 90. Per FIG. 11, the bottom of each basket may be formed with spaced apart bearing surfaces 96 that ride atop the rollers. A side rail 98 may be included to limit lateral movement of the baskets.

Figure 10:
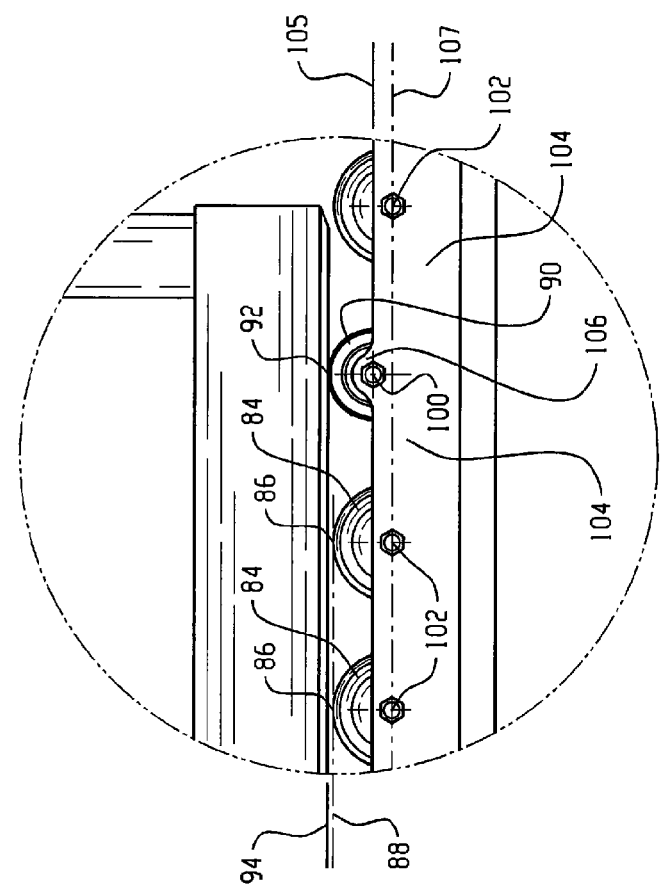
Figure 13:
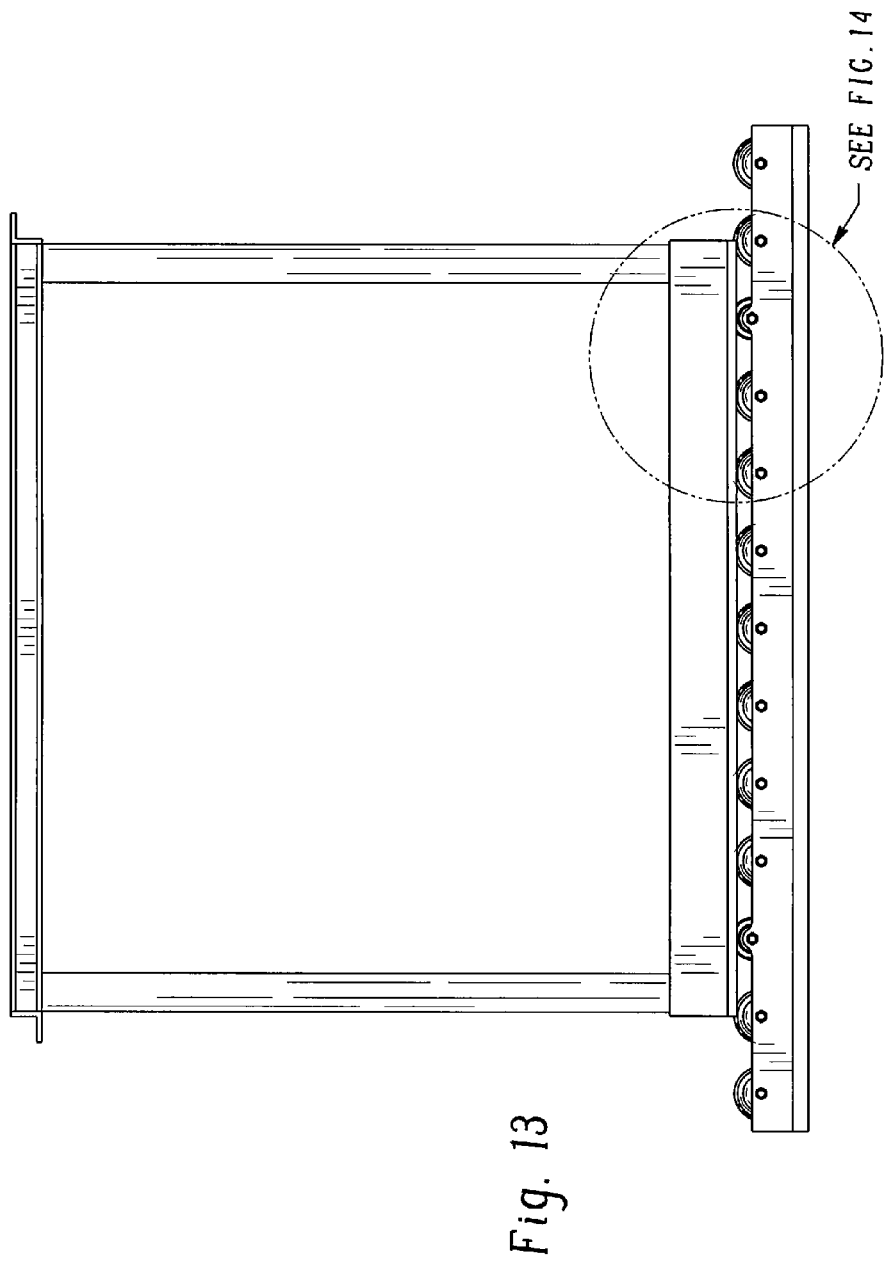
Figure 14:
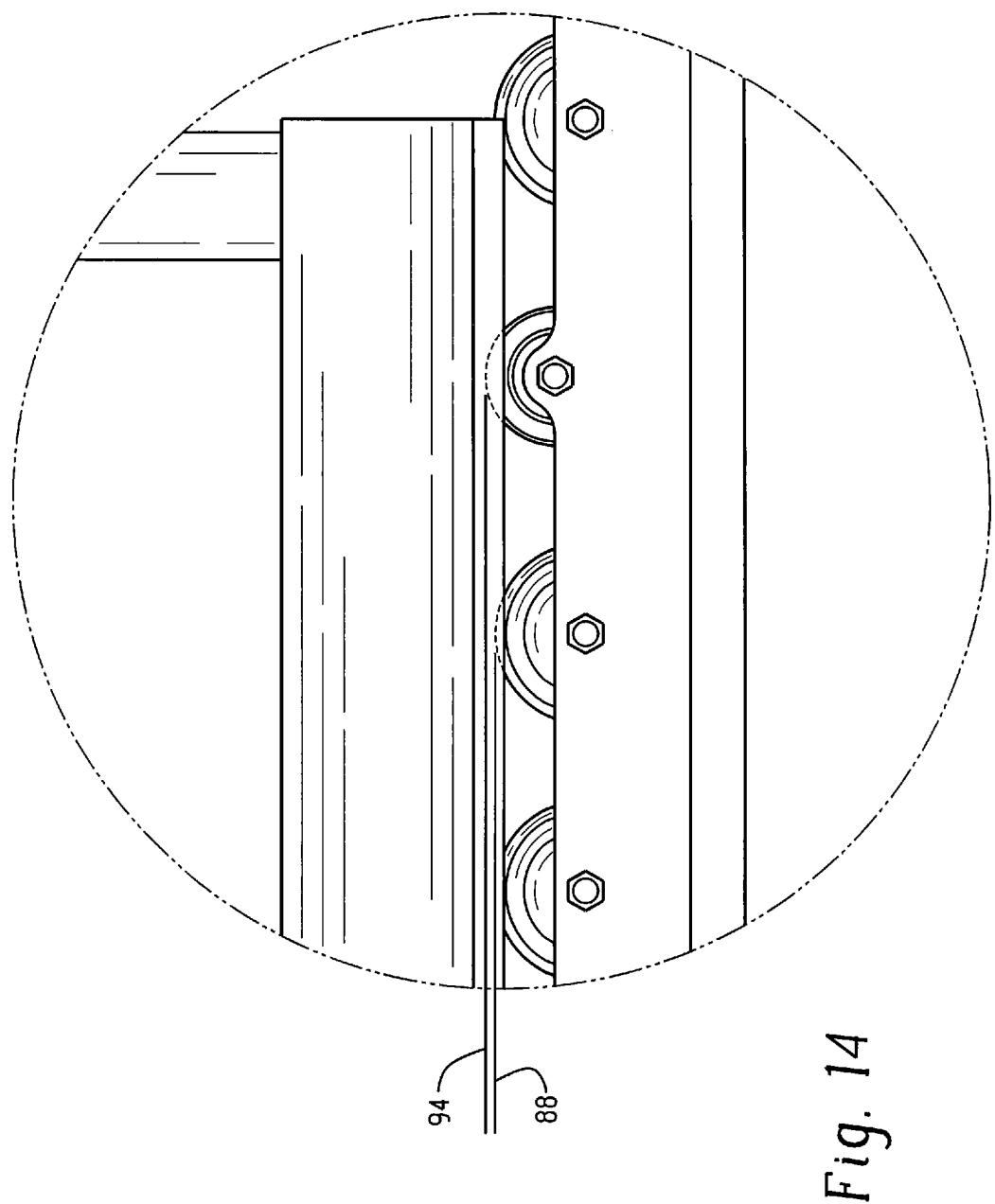
Figure 17:
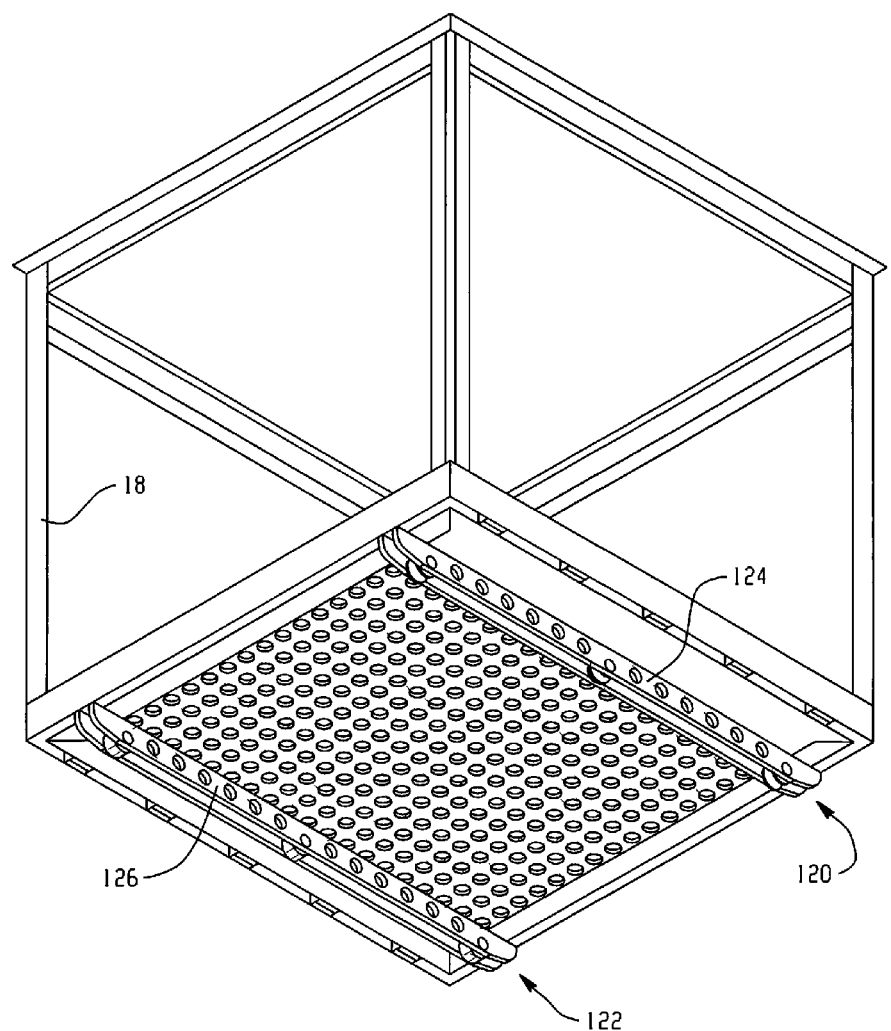

In the illustrated embodiment, the support rollers 90 have a smaller diameter than the transfer rollers 84, and the support rollers 90 are mounted on respective rotation axes 100 that lie in a plane 105 that is higher than a plane 107 in which the rotation axes 102 of the transfer rollers 84 lie. As shown in FIG. 10, the bracket or rail 104 that supports the rollers may have raised portions 106 to accommodate the higher axis of the support rollers. However, in another embodiment, the support rollers may have a larger diameter than the transfer rollers, and the support rollers and the transfer rollers may have respective rotation axes that lie in a common horizontal plane.

As shown in the embodiment of FIGS. 12-16, an alternative roller arrangement may include both the transfer rollers and support rollers. In one line 80 of the rollers the outer surfaces of both types of rollers are generally cylindrical, but in the other line 82 of rollers the outer surfaces of both types of rollers are formed with a V-groove 110 that receives a correspondingly shaped V-bracket 112 mounted on the bottom of the basket. The V-groove and V-bracket arrangement helps stabilize the baskets against lateral movement. In addition, the V-groove rollers are mounted on one side only so as to not over-constrain the basket and facilitate simpler retort guide rail installation without the precision that would be required if both lines of rollers had V-grooves and two V-brackets were used.

Referring now to the embodiment of FIGS. 17-20, the rollers are located on the bottom of the basket structure 18 as spaced apart lines of rollers 120 and 122, where both lines of rollers include both transfer rollers and support rollers. The rail structures 124 and 126 in which the rollers are mounted can, for example, be bolted or welded to the bottom of the basket frame. Transfer rollers 130 having external retort rail engaging surfaces 132 that define one horizontal plane 134 and support rollers 136 having external retort rail engaging surfaces 138 that define a horizontal plane 140 that is offset from, and lower than the horizontal plane 134 as seen in FIG. 18. In the illustrated embodiment, each transport roller 130 is located between two support rollers 136 to help support a product basket during loading and unloading into and out of a retort vessel. When the basket structure is positioned within a retort vessel for processing, only the support rollers 136 act to support the basket structure on the rail system of the retort vessel.

As best seen in the bottom view of FIG. 19, support rollers 136 of the line 120 of rollers and the line 122 of rollers are laterally paired with each other and transfer rollers 130 of two lines 120 and 122 are laterally paired with each other. Support roller 136 of line 120 may include a female V-shaped groove to ride on a V-shaped rail 170 mounted in the retort vessel (per FIG. 20), while support rollers 136 of line 122 may have a generally cylindrical external shape to ride on a flat rail surface 172 that is mounted in the retort vessel. Transfer roller 130 of line 120 may be have a male or female v-rail and roller combination external surface shape and transfer roller 130 of line 122 may have a cylindrical shape.

In one embodiment, the support rollers 136 have a diameter that is the same as a diameter of the transfer rollers 130, and the support rollers are mounted on respective rotation axes 150 that lie in a plane 154 and the transfer rollers are mounted on respective rotation axes 152 that lie in a plane 156 that is offset from and parallel to the plane 154. However, the support rollers could have a diameter that is different than a diameter of the transfer rollers, and the support rollers and the transfer rollers could have respective rotation axes that lie in a common plane.

It is to be clearly understood that the above description is intended by way of illustration and example only and is not intended to be taken by way of limitation, and that changes and modifications are possible.

What is claimed is:

1. A retort, comprising:
    a retort vessel; and
    a retort basket support assembly for supporting a retort basket during both transfer and reciprocating processing of the retort basket within the vessel, the assembly comprising:
        a roller arrangement;
        wherein the roller arrangement comprises:
            a plurality of transfer rollers having external surfaces that define a first horizontal plane;
            a plurality of support rollers having external surfaces that define a second horizontal plane that is offset from the first horizontal plane.

2. The retort of claim 1 wherein each transport roller is located between two support rollers to help support a product basket during loading and unloading.

3. The retort of claim 1 wherein the plurality of support rollers and the plurality of transfer rollers are arranged in first and second spaced apart rail assemblies to define a first line of rollers and a second line of rollers that is spaced apart from and runs parallel to the first line of rollers, the first line of rollers including both support rollers and transfer rollers and the second line of rollers including both support rollers and transfer rollers.

4. The retort of claim 3 wherein support rollers of the first line of rollers and the second line of rollers are laterally paired with each other and transfer rollers of the first line of rollers and the second line of rollers are laterally paired with each other.

5. The retort of claim 3 wherein the first rail assembly and second rail assembly are both mounted to a bottom of a retort basket structure such that the support rollers and transport rollers face downwardly from the retort basket structure and the second horizontal plane is lower than the first horizontal plane.

6. The retort of claim 3 wherein the first rail assembly and second rail assembly are both mounted within a retort vessel having an access door and a frame situated within the vessel for moving product baskets back and forth within the vessel, the frame defining a basket load zone, the first rail assembly and second rail assembly oriented such that the support rollers and transport rollers face upwardly and the second horizontal plane is higher than the first horizontal plane.

7. The retort of claim 1, wherein:
    the support rollers have a diameter that is the same as a diameter of the thetransfer rollers, the support rollers mounted on respective rotation axes that lie in a third plane and the transfer rollers mounted on respective rotation axes that lie in a fourth plane that is offset from and parallel to the third plane.

8. The retort of claim 1, wherein:
    the support rollers have a diameter that is different than a diameter of the transfer rollers, the support rollers and the transfer rollers having respective rotation axes that lie in a common plane.

9. A retort, comprising:
    a vessel having an access door;
    a frame situated within the vessel for moving a set of product baskets within the vessel, the frame defining a basket load zone for a plurality of product baskets;
    a support arrangement for supporting the product baskets within the vessel during movement of the frame, the support arrangement extending in a lengthwise direction of the vessel from a location toward a first end of the vessel to a location toward a second end of the vessel;
    a drive mechanism for reciprocating the frame back and forth in a reciprocating path that extends from the first end toward the second end of the vessel, the drive mechanism operates to reciprocate the frame at between 60 and 95 strokes per minute, where the stroke length is between about four inches and about eight inches.

10. The retort of claim 9 wherein the stroke length is between about five inches and about seven inches.

11. The retort of claim 10 wherein the stroke length is about six inches.

12. The retort of claim 11 wherein the drive mechanism operates to reciprocate the frame at between 80 and 95 strokes per minute.

13. A retort, comprising:
    a vessel having an access door;
    a frame situated within the vessel for moving a set of product baskets within the vessel, the frame defining a basket load zone for a plurality of product baskets;
    a support arrangement for supporting the product baskets within the vessel during movement of the frame, the support arrangement extending in a lengthwise direction of the vessel from a location toward a first end of the vessel to a location toward a second end of the vessel;
    a spray system for delivering heated fluid onto product baskets with the vessel;
    a drive mechanism for reciprocating the frame back and forth in a reciprocating path that extends from the first end toward the second end of the vessel, the drive mechanism configured to reciprocate the frame at between 80 and 95 strokes per minute as heated fluid is delivered, wherein the stroke length is between about five inches and about seven inches.

14. The retort of claim 13 wherein the frame includes a stop toward a first end of the vessel for abutting against one end of the set of product baskets within the vessel, the frame further including a latch mechanism toward a second end of the vessel for securing product baskets on the frame.

15. The retort of claim 14 wherein the latch mechanism includes:
- a latching part that is movable between a non-latching orientation and a latching orientation; and
- an actuator that operates to (i) move the latching part from the non-latching orientation to the latching orientation and (ii) maintain a bias of the latching part toward the latching orientation such that when a product basket engaged by the latching part moves toward the first end of the vessel as a result of a reciprocating operation, the latching part moves under the bias of the actuator to remain in engagement with the product basket and progressively reduce a spacing between the latching part and the stop as the set of product baskets shifts into a more compact arrangement during the reciprocating operation.

16. The retort of claim 15 wherein:
the latching part is pivotally mounted to the frame and includes a basket engaging surface portion for contacting an edge of the product basket when the latching part is in the latching orientation, the surface portion offset angularly from both first and second planes that define the edge of the product basket, where the first and second planes are perpendicular to each other and the surface portion is not parallel to either of the first and second planes.

17. The retort of claim 16 wherein:
the latch mechanism includes a first plate connected for movement with the latching part and a second plate connected for movement with the latching part, the second plate spaced apart from the first plate,
the actuator comprises a first bladder, a second bladder, and an intermediate plate between the first and second bladder, the intermediate plate connected to the frame and extending between the first plate and the second plate, the first bladder located between the first plate and the intermediate plate, the second bladder located between the intermediate plate and the second plate,
when the first bladder is expanded and the second bladder is collapsed, the first bladder causes a spacing between the intermediate plate and the first plate to enlarge and a spacing between the intermediate plate and the second plate to reduce such that the latching part moves to the latching orientation,
when the first bladder is collapsed and the second bladder is expanded, the second bladder causes the spacing between the intermediate plate and the second plate to enlarge and the spacing between the intermediate plate and the first plate to reduce such that the latching mechanism moves to the non-latching orientation.

* * * * *